US009126162B2

(12) United States Patent  (10) Patent No.: US 9,126,162 B2
Simmat et al.  (45) Date of Patent: *Sep. 8, 2015

(54) POSITIONING UNIT FOR A FUNCTIONAL UNIT

(75) Inventors: Olaf Simmat, Dornburg (DE); Andreas Vester, Jena (DE); Patrick Heinrich, Jena (DE)

(73) Assignee: Quantifoil Instruments GmbH, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/635,901

(22) PCT Filed: Mar. 16, 2011

(86) PCT No.: PCT/EP2011/053956
§ 371 (c)(1),
(2), (4) Date: Sep. 18, 2012

(87) PCT Pub. No.: WO2011/113858
PCT Pub. Date: Sep. 22, 2011

(65) Prior Publication Data
US 2013/0011224 A1  Jan. 10, 2013

(30) Foreign Application Priority Data
Mar. 18, 2010 (DE) .......................... 10 2010 011 899

(51) Int. Cl.
*B01L 9/00* (2006.01)
*B01F 11/00* (2006.01)
(Continued)

(52) U.S. Cl.
CPC ....... *B01F 11/0008* (2013.01); *B01F 15/00733* (2013.01); *B01L 9/523* (2013.01); *B01L 7/52* (2013.01); *B01L 2200/025* (2013.01); *G01N 35/028* (2013.01); *G01N 2035/00524* (2013.01)

(58) Field of Classification Search
CPC .................................. B25B 5/142; B01L 9/523
See application file for complete search history.

(56) References Cited

U.S. PATENT DOCUMENTS 1,221,601 A * 4/1917 Rowland ........................ 269/109
2,599,833 A   6/1952 Holmlund et al.
(Continued)

FOREIGN PATENT DOCUMENTS

DE     44 19 480      12/1995
DE    101 34 702       2/2003
(Continued)

OTHER PUBLICATIONS

International Preliminary Report on Patentability dated Mar. 18, 2010, issued in International Application No.: PCT/EP2010/053556 (English Translation).
(Continued)

*Primary Examiner* — P. Kathryn Wright
(74) *Attorney, Agent, or Firm* — Knobbe Martens Olson & Bear LLP

(57) ABSTRACT

An apparatus for positioning a functional device, wherein the apparatus has a main body, a carrier element that can be disposed on the main body to receive the functional device, positioning stops, which are mounted displaceably to clamp the functional device, an actuating device which is adapted such that, by actuating the actuating device, the positioning stops can be transferred between an operating state engaging the functional device and an operating state releasing the functional device, and a force transmitting element which is adapted to transmit an actuating force from the actuating device to the positioning stops, wherein the actuating device and the force transmitting element are coupled in such a manner that, in the operating state engaging the functional device, the force transmitting element transmits a functional device force of the functional device to the actuating device in such a manner that the actuating device remains in a rest position with respect to the carrier element, in spite of the action of the transmitted functional device force.

18 Claims, 13 Drawing Sheets

(51) Int. Cl.
*B01F 15/00* (2006.01)
*B01L 7/00* (2006.01)
*G01N 35/02* (2006.01)
*G01N 35/00* (2006.01)

(56) References Cited

U.S. PATENT DOCUMENTS

| | | | |
|---|---|---|---|
| 6,514,465 B2 | 2/2003 | Steiner | |
| 7,054,001 B2 * | 5/2006 | Geiger | 356/244 |
| 7,070,740 B1 | 7/2006 | Matson et al. | |
| 7,832,921 B2 | 11/2010 | Malin | |
| 2002/0098115 A1 | 7/2002 | Fawcett et al. | |
| 2003/0017083 A1 | 1/2003 | Pobering et al. | |
| 2007/0020152 A1 | 1/2007 | Costello, III et al. | |
| 2010/0218620 A1 * | 9/2010 | Hoyer et al. | 73/863.11 |

FOREIGN PATENT DOCUMENTS

| | | |
|---|---|---|
| DE | 10 2004 021 664 | 12/2005 |
| DE | 10 2004 043 883 | 3/2006 |
| DE | 10 2010 011 899 | 9/2011 |
| EP | 1 111 391 | 12/1999 |
| EP | 1 186 891 | 9/2000 |
| EP | 1 393 797 | 8/2003 |
| EP | 1 721 964 | 5/2006 |
| GB | 1 447 643 | 8/1976 |
| WO | WO 86/00732 | 1/1986 |
| WO | WO 86/07232 | 12/1986 |
| WO | WO 99/13339 | 3/1999 |
| WO | WO 99/15905 | 4/1999 |
| WO | WO 01/96880 | 12/2001 |
| WO | WO 2004/003504 | 1/2004 |
| WO | WO 2007/103963 | 9/2007 |
| WO | WO 2008/135565 | 11/2008 |
| WO | WO 2010/106147 | 9/2010 |

OTHER PUBLICATIONS

International Search Report dated May 31, 2010, issued in International Application No.: PCT/EP2010/053556.

International Search Report dated Jun. 30, 2011, issued in International Application No.: PCT/EP2011/053956.

* cited by examiner

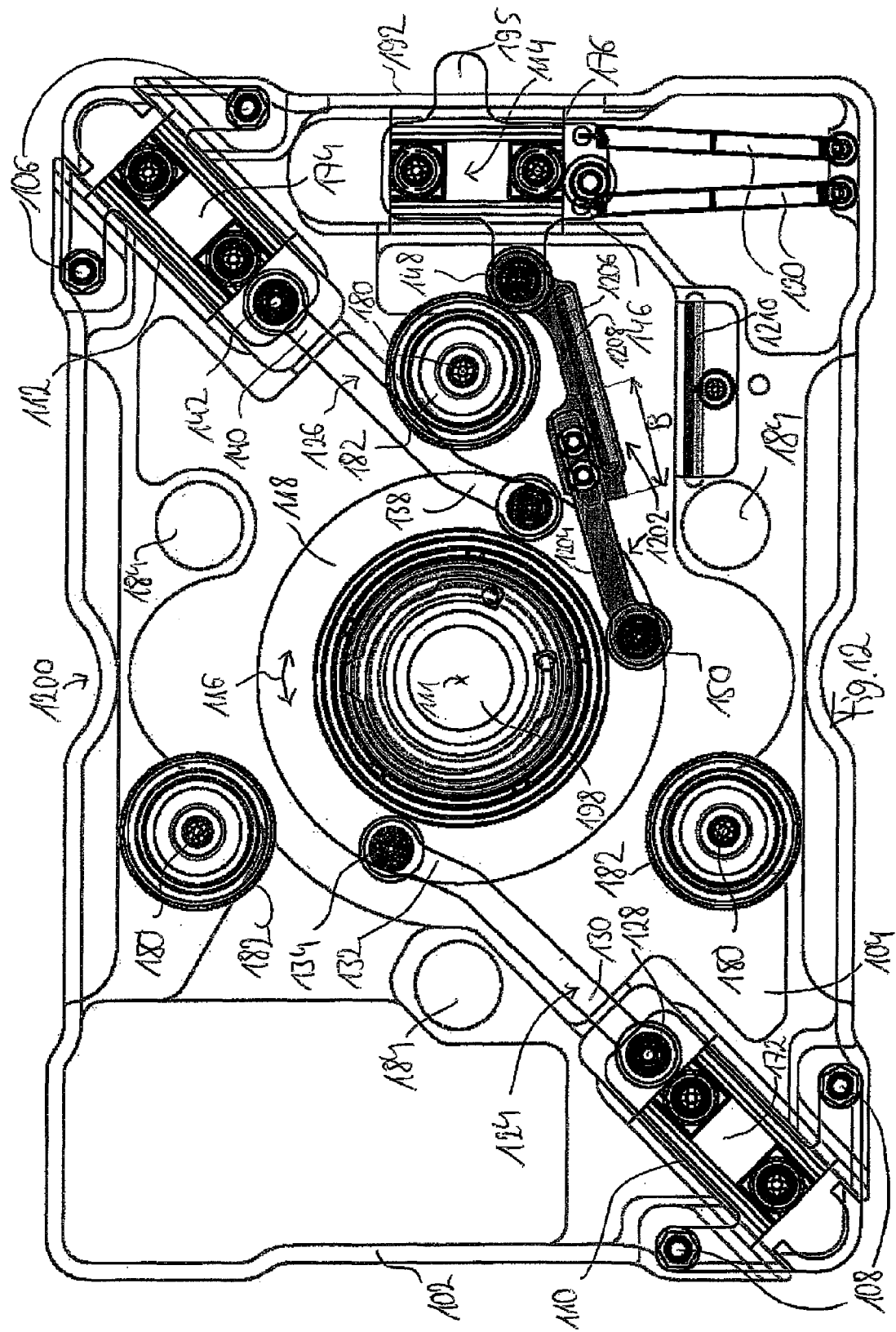

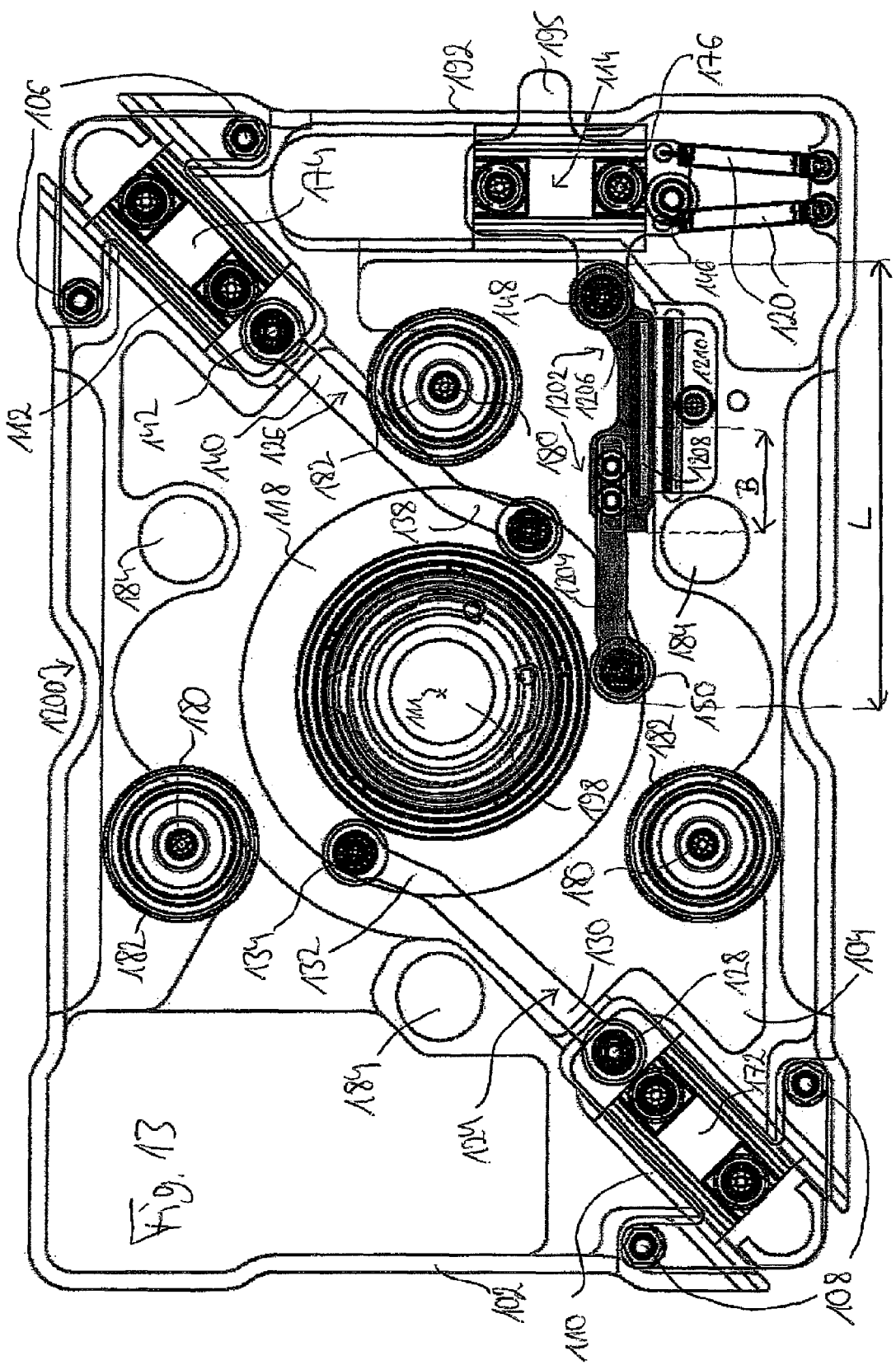

POSITIONING UNIT FOR A FUNCTIONAL UNIT

RELATED APPLICATIONS

This application is a U.S. National Phase of International Application No. PCT/EP2011/053956, filed Mar. 16, 2011, designating the U.S. and published on Sep. 22, 2011 as WO 2011/113858, which claims priority to German Patent Application No. 10 2010 011 899.0, filed Mar. 18, 2010. The content of each of these applications is incorporated herein by reference in its entirety.

The invention relates to an apparatus for positioning a functional device.

The invention further relates to a method for positioning a functional device.

The microtiter plate has been established as standard for the simultaneous processing of a large number of small sample volumes in molecular biology. A microtiter plate is a rectangular plate of fixed dimensions, which contains a defined number of isolated cavities (wells) in rows and columns. Inside these wells different samples can be tested for their properties independently of one another. Microtiter plates having 96, 384, or 1536 wells are usually widely used in pharmaceutical, chemical, and biological research.

With an increasing degree of automation and the increase in the number of wells in a microtiter plate, there is a tendency to automate filling processes and further processes. Various types of pipetting heads are known for simultaneously filling the wells and can receive a number of pipetting tips corresponding to the number of wells.

The greater the number of wells in the corresponding microtiter plate, the smaller the diameter of each of these indentations. The demands placed on the positioning accuracy of microtiter plate to pipetting head therefore increase. Furthermore, in a large number of applications in pharmaceutical, chemical, and biological research it is necessary to ensure thorough mixing of the components in the wells of the microtiter plate. A simple possibility for influencing the local concentration and therefore the probability of interaction of the reaction partners is an external energy input by defined movement (shaking) of the reaction container. The advantage of such a method is the freedom from contamination as a result of the non-contact energy input (in contrast to methods using moved mixing tools). Furthermore, due to this mixing movement of a shaking apparatus, the homogenization of the temperature within the sample is also accelerated with respect to naturally occurring compensating processes.

Manufacturing tolerances in the production of microtiter plates in length, width, and web height have a direct effect on the positioning of the microtiter plate since the microtiter plate is conventionally frequently displaced by springs toward solid obstacles.

In case of conventional systems, positioning pieces are often securely attached for fixing microfilter plates during the process of pipetting or shaking, the object of these positioning pieces being to always hold the microtiter plate in position. Springs can be contained in these positioning pieces. However, the spring force produced should be so great that the microtiter plate is held in position against the centrifugal force produced by the orbital mixing movement. Due to the high force required, the insertion of the microtiter plates into the shaking apparatus by the transporting apparatus (for example a gripper arm) of a robot may be difficult or impossible depending on the circumstances. The microtiter plate may move during the shaking process and this may consequently lead to undesired movements of a positioning apparatus.

EP 1,186,891 discloses that in order to enable the spatial alignment of a support plate, this has a joint head on the underside which lies in a joint socket of a support plate. A connection piece of the joint head is guided through a central opening in the joint socket and bears a clamping ring abutting against the outer side of the joint socket and which can be pressed by means of a flange that can be tightened for fixing the alignment of the support plate. Two diagonally outwardly displaceable centering stops located opposite one another in a mirror-inverted manner on the upper side of the support plate are fastened to diagonally displaceable sliders. These engage at the opposite ends of a rotatable coupling lever with said lever. This lever sits on a vertical shaft, which extends from the underside of the support plate through a hole in the joint head as far as the end of the connection piece. There, said lever carries an actuating lever which can be rotated against the restoring force of a spiral spring for movement of the centering stops outward to allow a lowering or lifting of a microtiter plate.

WO 86/07232 discloses an apparatus for positioning a circuit panel.

EP 1,111,391 discloses a device for holding an item, in particular a microtiter plate, comprising a laying surface, wherein a stop limiting the displacement of the item on one side in the plane of said item is provided in the area of the laying surface, as well as a clamping apparatus having a clamping part that can be retracted with respect to the stop against a prestress.

DE 10 2004 021 664 discloses a microtiter plate shaking apparatus comprising a vibratory plate which has a reception zone for a microtiter plate and positioning pieces disposed thereon for the microtiter plate to be held. At least one positioning piece is movably mounted and can be moved between a working position and a release position. The at least one movably mounted positioning piece is movable from the working into the release position by means of a drive.

WO 99/13339 discloses a positioning apparatus for positioning a microtiter plate. A positioning platform can be provided in a surrounding platform. A further platform can be provided in the positioning platform. The surrounding platform has actuators. A movable carrier platform of the positioning platform can be moved relative to the carrier platform. In this case, bulk-like elements are disposed along the longitudinal side between the innermost further platform and the surrounded positioning platform. By means of a fluid, such as compressed air for example, the bulk-like elements can absorb the fluid or blow out the fluid so that a movement and positioning of the inner surrounded platform can thereby be implemented.

DE 4419480 discloses an apparatus for holding articles in place on shaking devices, which have a movable shaking table with a flat positioning surface for the articles, characterized by the arrangement of a flat formed part made of a flexible material with a high friction coefficient, in particular ethylene propylene rubber, which is placed freely on the positioning surface of the shaking table and is fixed by friction and, by means of friction, fixes the articles applied to the side face remote from the shaking table.

EP 1,721,964 discloses a storage device for laboratory samples, comprising a shaker drive, a rack carrier driven by said shaker drive for performing a shaking motion with horizontal component, and at least one storage rack disposed on the rack carrier, said storage rack comprising storage locations for a plurality of laboratory samples on top of each other, characterized by a compensating weight assembly connected to an upper end portion of the storage rack and driven to exert, on the upper end portion, a force opposite to the shaking motion in order to thus counteract an oscillation, caused by the shaking motion, of the upper end portion of the storage rack.

EP 1,393,797 discloses a shaking and mixing apparatus, comprising an electric drive, an eccentric unit driven by the drive and a vessel holder moved by the eccentric unit and designed to receive the vessels to be moved by the shaking and mixing apparatus, characterized in that the common center of gravity of the vessel holder and of vessels is located in a plane oriented parallel to the eccentric movement, said plane being only slightly vertically spaced from the plane oriented parallel to the eccentric movement, in which the center of gravity of the eccentric unit lies.

DE 10 2004 021 664 discloses a microtiter plate shaking apparatus comprising a vibratory plate which has a reception zone for a microtiter plate and positioning pieces disposed thereon for the microtiter plate to be held, characterized in that at least one positioning piece is movably mounted and can be moved between a working position and a release position, and in that the at least one movably mounted positioning piece is movable from the working position into the release position by means of a drive.

DE 10 2004 043 883 discloses a sample bottle, in particular a milk sample bottle, comprising a bottle body, in which a receiving chamber is formed to receive a sample, a first cover which is disposed on the bottle body and which is used to close the receiving chamber, wherein a first through-opening is formed in the first cover in the receiving chamber, a second cover which comprises a second through-opening, wherein at least part of the second cover can be moved, interacting with the first cover, in a direction of operational movement such that said movement enables both of the through-openings to be placed in an at least partially overlapping manner and/or to be displaced at least partially from said overlapping, and a locking device which locks a movement of the second cover which is counter to the direction of operational movement.

It is still difficult to position a functional device precisely and to protect a positioning device against undesirable influences under mechanical load, in particular during a shaking operation.

It is the object of the present invention to position a functional device precisely and to protect a positioning device against undesirable influences under mechanical load.

This object is achieved by an apparatus for positioning a functional device and by a method for positioning a functional device having the features according to the independent claims.

According to one exemplary embodiment of the present invention, an apparatus for positioning a functional device (for example a carrier plate, in particular a sample carrier plate, more particularly a rectangular sample carrier plate) is created. The apparatus has a main body (for example a base body substantially cuboid in shape, on and/or in which at least some of the remaining components of the apparatus are disposed) and a carrier element that can be disposed (or is disposed) on the main body for receiving (in particular directly) the functional device (for example a base surface of the functional device). Positioning stops are mounted displaceably (for example linearly displaceably by means of a guide rail, or otherwise displaceable diagonally together, outwardly or inwardly in a mirror-inverted manner) to clamp the functional device. An actuating device is provided that is designed in such a manner that, by actuating the actuating device, the positioning stops can be transferred between an operating state engaging the functional device and an operating state releasing the functional device (wherein, in the releasing operating state, the positioning stops are further from the center of the carrier element than in the engaging operating state). A (for example rotatably mounted) force transmitting element (for example a circular disk) may be adapted to transmit (in particular deflect or other conversion of force) an actuating force from the actuating device to the positioning stops. The actuating device and the force transmitting element are coupled in such a manner that, in the operating state engaging the functional device, the force transmitting element transmits a functional device force of the functional device onto the actuating device in such a manner that the actuating device remains substantially in a rest position with respect to the carrier element, in spite of the action of the transmitted functional device force.

According to another exemplary embodiment of the present invention, a method is provided for positioning a functional device. With the method, the functional device is disposed between positioning stops mounted displaceably on a carrier element in an operating state releasing the functional device to receive the functional device on the carrier element, wherein the carrier element can be disposed on a main body. The functional device is further clamped between the positioning stops by actuating an actuating device to transfer the positioning stops from the operating state releasing the functional device into an operating state engaging the functional device. An actuating force is transmitted from the actuating device to the positioning stops by means of a force transmitting element. A functional device force of the functional device is transmitted from the force transmitting element to the actuating device in the operating state engaging the functional device, in such a manner that the actuating device remains in a rest position with respect to the carrier element, in spite of the action of the transmitted functional device force.

In particular, a "functional device" can be understood to be any physical device that can be positioned in the positioning device in a location-defined manner to provide an assigned function. In particular, the functional device may be a carrier plate, for example a sample carrier plate, such as a microtiter plate. Alternatively, the functional device may for example be a storage or receiving container disposed in a grid-like manner, which for example may be equipped with disposable pipette tips or needles or similar aids.

In particular, a "carrier element" on the main body may be understood to be a component of the apparatus that moves together with a clamped functional device. By contrast, the main body may be at rest in a laboratory system. The main body can be placed on an underlying surface (for example a table plate) and may remain at rest thereon.

In particular, a "functional device force" may be understood to be a force that a functional device exerts onto the positioning stops in the state clamped between positioning stops. Such a force may be produced in particular by an acceleration force generated by a shaking movement, said acceleration force being applicable to the functional device to mx fluid samples received therein. In particular, the actuating device and the force transmitting element can be coupled in such a manner that, in the operating state engaging the functional device, the force transmitting element transmits a functional device force of up to 50 N to the actuating device, without the actuating device being moved.

In particular an "actuating force" can be understood to be a muscular force of a user or a force of an electric control unit that is exerted onto the actuating device so as to transfer the actuating device between the operating state releasing the functional device and the operating state engaging the functional device. Such an actuating force can be actively applied by a user or an electric control unit, or can be passively generated as a result of a previously deflected spring returning into its starting position by releasing the actuating device, wherein the spring may optionally be prestressed. In other words, such an actuating force may be exerted actively or passively. The application of an actuating force of at most 10 N may be sufficient to transfer the positioning stops between the two aforesaid operating states.

According to one exemplary embodiment, a positioning device is created for a functional device, in which a clamping or unclamping of a functional device on a carrier element or positioning stops disposed thereon is enabled by an actuating device that can be actuated with low force. Due to a simple displacement operation, the positioning stops can be distanced from one another by a force transmission mechanism so that a receiving chamber can be enlarged and a functional device can be inserted. After insertion, a return of the positioning stops into another spaced position can be achieved by a return movement of the actuating device, whereby the functional device is engaged by the positioning stops. If an external or internal force, for example generated by a shaking device or the like integrated into the main body, acts on the received functional device, an undesired movement to and fro of the actuation device is thus prevented in accordance with the invention, since, in the engaging operating state, such a mechanical functional device force on the actuating device is coupled in such that it does not lead to a movement of the actuating device. This can be implemented by an asymmetrical force transmission characteristic from the actuating device to the positioning stops and also from the positioning stops to the actuating device. In other words, the exertion of a force on the actuating device causes a deflection of the positioning stops that is greater than a deflection of the actuating device when the same force is exerted onto the positioning stops. With functional device forces normally occurring during shaking processes, a resultant blocking of the movability of the actuating device cannot be overcome by the functional device forces. The elimination of a movement of the actuating device due to a force starting from the functional device allows fail-safe operation of the apparatus, since a movement to and fro of the actuating device can thus be avoided. This ensures that the functional device cannot fall out of the positioning stops as a result of an undesired movement of the actuating device. Further, a constantly high positioning accuracy can be achieved due to the inhibition of a transmission of movement from the positioning stops to the actuating device. With conventional functional device forces of the functional device, which are produced by shaking at a frequency of 1000 revolutions per minute for example, a resultant forces leads to the actuation device remaining at rest. This reliably prevents the actuating device from opening, at least in part, as a result of an undesired movement of the actuating device due to the shaking, whereby the functional device would therefore be brought out of engagement with the positioning elements. In such an undesired situation, the functional device could therefore leave the apparatus at high speeds or could at least move uncontrollably therein. It is exactly this that is reliably prevented by the transmission of force according to the invention. This increases the operational reliability of the apparatus and the precision of the clamping of the functional device in the apparatus. A high degree of positioning accuracy before, during and after a shaking procedure is important, particularly with use of an automatic pipetting device having a matrix-like arrangement for example of ceramic needles.

Such an asymmetrical force transmission characteristic (from the actuating device to the functional device or vice versa) can be achieved by different mechanical designs. According to one exemplary embodiment, this is implemented by coupling in a force from the functional device to the actuating device in a direction of action that is incompatible with a direction of displacement of the actuating device, and in particular is oriented perpendicular thereto. According to an alternative embodiment, a merely uni-directional transmission of force could be implemented by a one-way clutch (known from the field of bicycle technology to achieve freewheeling).

Additional exemplary embodiments of the apparatus are described hereinafter. These are also valid for the method.

In one exemplary embodiment, the apparatus has a movably mounted coupling rod, by means of which the actuating device is coupled to the force transmitting element. The positioning stops can be transferred between the operating state engaging the functional device and the operating state releasing the functional device by moving the coupling rod. The coupling rod can thus be moved (in particular pivoted) between a first position and a second position in such a manner that a force can be transmitted from the actuating device to the positioning stops. On the other hand, the transmission of force may not occur in at least in one of the positions, and therefore a movement of the positioning stops leads to a movement of the actuating device. For example, a coupling rod may be displaced transversely for this purpose. In particular, a configuration is possible in which the coupling rod is pivoted between the two positions, since efficient adaptation of an effective power arm is possible as a result of a pivoting motion.

Further, the apparatus may have a linear guide device for defining a direction of linear displacement. Any direction along which the actuating device is exclusively displaceable can be referred to as a direction of linear displacement. In other words, such a linear displacement device can define the direction along which the actuating device can be actuated, wherein actuation in a direction perpendicular thereto is not possible. In the operating state engaging the functional device (which can occur without action of external forces), the coupling rod can be oriented in such a manner that the functional device force can be transmitted to the actuating device in a manner acting substantially perpendicular to the direction of linear displacement. If the functional device force, that is to say a force starting from or produced by the sample carrier, is transmitted to the actuating device such that the force acts (approximately) perpendicular to the direction of linear displacement, no force component that would lead to a movement of the actuating apparatus is thus (approximately) transmitted. This is due to the fact that the actuating device can be mounted in the linear displacement device such that displacement is only possible in the direction of linear displacement, but not in other directions.

The device may have further movably mounted coupling rods, by means of which the positioning stops can be coupled to the force transmitting element. The positioning stops can be transferred between the operating state engaging the functional device and the operating state releasing the functional device by moving, in particular by pivoting, the further coupling rods. Furthermore, the device may have further linear guide devices for defining further directions of linear displacement of the positioning stops, the positioning stops being displaceable exclusively along said further directions of linear displacement. An extension of the further coupling rods may be aligned with the further directions of linear displacement. The further coupling rods can be oriented in such a manner that the actuating force is transmitted to the positioning stops in a manner acting substantially parallel to the further directions of linear displacement. Coupling in of a (positive or negative) actuating force carried out substantially parallel to the further directions of linear displacement ensures an effective low-force coupling-in of force in the direction of action from the actuating device to the positioning stops. By contrast, in the reverse direction of action from the positioning stops to the actuating device, the introduction of force is oriented so as to inhibit movement where possible, that is to say is ideally oriented perpendicular to the direction of linear displacement of the actuating device. This asymmetrical force coupling ensures the desired fixing of the functional device, even during a shaking process.

A further linear guide element may thus be assigned to each of the positioning stops, and the respective positioning stop may be mounted linearly displaceably in or on said linear guide element. Such a linear guide element may have a slot, along which a pin can slide so as to enable displacement of the respective positioning stop toward the centrally disposed force transmitting element or away from the force transmitting element. If a positioning stop moves toward the center or another defined target point, the other positioning stop thus also moves due to the force coupling toward the center. On the other hand, a positioning stop moves away from this center when the other positioning stop moves away from the center.

These further linear guide elements can be oriented such that the positioning stops are mounted displaceably parallel to one another. For example, this can be achieved if the linear guide grooves in the further linear guide elements are oriented so as to extend substantially parallel to one another so that, when they move, the positioning stops are displaced parallel to one another.

The further linear guide elements assigned to the positioning stops can be oriented in particular such that the positioning stops are mounted displaceably, either offset identically or offset in parallel relative to a diagonal of the carrier element. In other words, in accordance with this exemplary embodiment, the positioning stops in the linear guide elements move parallel to one another, but optionally with a predefined lateral offset. The positioning stops do not move precisely in the direction of a midpoint of the carrier element, but miss the midpoint by a predefined lateral offset, for example in the tangential direction, with continued movement. A leverage can thus be transmitted efficiently between the force transmitting element and the positioning stops, which can lead to rotation of the force transmitting element and therefore to an efficient transmission of force. A tangential offset is not obligatory, since the movement can be linear. In one exemplary embodiment, the linear displacement elements only move linearly in the direction of displacement. If the diagonals were to pass through the midpoint, it would be advantageous for the deflection points of the coupling rods at the coupling disk to lie outside the diagonals so as to generate a power arm and therefore a torque. The provision of an offset is not generally obligatory and applies for example to rectangular sample plates. For example, in the case of a square sample plate, they move through the midpoint over the diagonals, that is to say without offset.

The actuating device can have a slider for manual actuation of the actuating device by a user. Such a slider can also be guided in a linear guide groove in the linear guide device, that is to say for example by means of a displaceable pin, which can be displaced in an elongated groove in a predefinable direction. A user is therefore protected from incorrect operation of the apparatus since such an actuating device only enables a forward or backward movement for transferring the system between the two operating states.

The slider can have a gripping piece, which can be formed in order to intuitively show a user that this is a gripping piece. For example, such a gripping piece can have a pin-shaped end portion at which a user can grip the actuating device. Both a pushing and a pulling are possible with such a pin-shaped end portion.

For example, the coupling rod or each of the further coupling rods may have a first portion extending in a straight line and a second portion extending in a straight line, wherein the first portion extending in a straight line and the second portion extending in a straight line can be angled with respect to one another. The first portion extending in a straight line may transition directly into the second portion extending in a straight line. A rounding in a boundary region is possible. Such an angled leaver arm allows a particularly space-saving and effective transmission of the forces or transfer of the coupling rod between the different operating states of the apparatus.

The direction of linear displacement assigned to the actuating device may extend parallel to a lateral delimiting edge of the carrier element. Such a geometric arrangement allows particularly user-friendly actuation, since the actuating device remains easily accessible, even when the functional devices have been inserted. In addition, an extension of the direction of linear displacement along an edge is very compatible with the desired coupling-in of force in an asymmetrical manner.

The actuating device may correspondingly be disposed at a side region of the carrier element between two adjacent corner regions of the carrier element. In such a configuration, a region between the corners of the carrier element can be used so as to implement there the actuating device in a space-saving manner without significantly reducing the surface area usable to receive the functional device. One-dimensional sliding of the actuating device along such a side region likewise makes it possible to achieve a uni-directional transmission of force at low constructional cost, as described above.

Alternatively, however, it is also possible to dispose the actuating device in a corner region of the carrier element and to thus arrange the direction of linear displacement substantially from such a corner region toward a center of the carrier element. Other geometries, such as the arrangement of the actuating device on an underside of the device or in a central region of the main carrier are likewise possible.

The apparatus may have a clamping device disposed between the carrier element and the actuating device, said clamping device being designed to transmit a mechanical force to the actuating device. In particular, such a clamping device may directly bridge a region between the carrier element and the actuating device. The clamping device, which for example may have one or more springs, in particular a helical spring, can prestress the actuating device, for example in a position (deflected position) that corresponds to the releasing operating state of the apparatus. The clamping device may thus have a tendency to drive the actuating device back into the engaging operating state. The clamping device thus constitutes protection against an undesired falling out of a clamped functional device from the apparatus. If a user therefore does not exert any force onto the actuating device, the positioning stops engage a received functional device and the clamping device may be in a force-free state. Only when the actuating device is deflected against a restoring clamping force of the clamping apparatus as a result of a muscular force of a user or an actuating force of a robot is the actuating device displaced, which then leads to a transfer of the positioning stops into the state releasing the functional device due to the above-described force transmission mechanism. So that the functional device remains securely held by the positioning stops after insertion, the clamping device draws the functional device back into the engaging operating state once the muscular force or the actuating force of the robot has been removed.

In particular, one end of the clamping device, that is to say a spring end, may be disposed in a corner region of the carrier element. Another end of the clamping device may then be connected directly to a slider of the actuating device.

In particular, the clamping device may have a plurality, for example two, springs disposed parallel to one another. This further increases the stability or reliability of the tendency of the return into the engaging state of the apparatus in the force-free situation.

According to one exemplary embodiment of the invention, the actuating device and the force transmitting device can be coupled in such a manner that, in the operating state engaging the functional device, the force transmitting element transmits an acceleration force produced by a shaking device to the actuating device in such a manner that the actuating device remains substantially in a rest position, in spite of the action of the transmitted acceleration force. In other words, according to such an exemplary embodiment, it can be made possible that the actuating device can be actuated for clamping or unclamping the functional device in relation to positioning stops so that, in this direction of action, a corresponding force can be transmitted efficiently from the actuating device to the positioning stops so as to displace the positioning stops. Simultaneously however, after the clamping of the positioning stops, such a coupling position of the actuating device relative to the force transmitting element can be brought about since an introduction of force leading to a movement of the actuating device in the reverse direction of action, that is to say acting on the actuating device, is mechanically blocked. This can be accomplished by deflecting an acceleration force having such a direction onto the actuating device so that this is oriented orthogonally to a, for example linear, direction of displacement of the actuating device. A "direction of displacement" can be understood in this context as an axis along which the actuating device can be displaced by a user or a robot, whereas a displacement along other axes, in particular along an axis perpendicular to the direction of displacement, is prevented.

In particular, the actuating device and the force transmitting element (in particular formed as a coupling disk) can be coupled by means of the coupling rod connecting them in a bridged manner, in such a way that, in the operating state engaging the functional device, this coupling rod couples in the shaking force substantially perpendicular to a direction of displacement of the actuating device. The coupling rod can be brought into different orientations to the direction of displacement of the actuating device. In an angular or oblique position between the coupling rod and the direction of displacement, at least one force component different from zero can act in the direction of displacement so that a transmission of force is possible. In an orthogonal or at least substantially orthogonal position (that is to say differing from a right angle by a few degrees) between the coupling rod and the direction of displacement, no force component (or at least none overcoming any static friction) can act in the direction of displacement, and therefore movement is blocked. Such a configuration therefore enables on the one hand a clamping of the functional device by means of low-force actuation of the actuating device, and on the other hand, when the functional device is clamped, inhibits a return transmission of a force, in particular triggered by a shaking movement of a shaking plate, to the actuating device.

The positioning stops, the actuating device and the force transmitting element can be disposed on the carrier element and can be movable jointly with respect to the main carrier. The carrier element may be formed as a plate having two opposed main surfaces, wherein the positioning stops can be disposed on one of these main surfaces and the actuating device and the force transmitting element can be disposed on the other of these main surfaces. The carrier element can therefore be provided so as to be removable from the main body. The functional components can therefore be disposed adjacent to the main body so as to be protected against external influences.

An eccentrically mounted shaft (eccentric shaft) can be disposed rotatably on the main body and engages in a recess in the force transmitting element of the carrier element and can be driven so as to exert an orbital shaking movement of the main body. In particular, a central circular recess in a force transmitting element formed as a coupling disk may be provided, in which an eccentrically rotating cylindrical shaft can engage to transmit an orbital shaking or mixing movement.

One or more recesses, each with a magnet element provided therein, may be formed in the main body. One or more bolts of the carrier element, each having a magnet element provided thereon, can be received in the one or more recesses. The main body can be fastenable on the carrier element by means of an attracting force between the magnet elements of the carrier element and the magnet elements of the main body. A contactless, magnetic fastening of the carrier element on the main body can thus be achieved, which can be operated intuitively by a user. A corresponding form coding, which results from the relative arrangement between the bolts and recesses, further prevents incorrect assembly.

At least some of the bolts may have one or more resonance damping elements, in particular resilient rings, which press in the recesses against the main body in the event of a resonant shaking movement (and only then) so as to bring the apparatus out of resonance. In undesirable conditions, in particular during operation at an unfavorable shaking frequency, a build up in the apparatus may occur so that it is subject to resonance vibration, which is undesirable. In this resonance state, the resonance damping elements, which for example may be formed as rubber rings that are coated to minimize friction, are pressed laterally against the inner surface of the recesses. This damps the vibration, whereby the system can again be brought out of resonance. A self-regulating system can thus be created using means of simple design.

A plurality of (in particular three) spherical seats with balls (in particular three) disposed therein can be formed in the main body, the carrier element resting on said balls. In accordance with one exemplary embodiment, the balls may be the only contact points of the carrier element, which guarantees low-friction and therefore low-energy operation. The contact points of the balls on the upper side and lower side can engage with a material surface, either on one side or on both sides, said material surface cooperating with the material of the balls with little friction.

A movable machine element, for example a servo lever, may be disposed on the main body (or alternatively on the carrier element), wherein the actuating device can be actuated by guiding, for example pivoting, the movable machine element in a machine-controlled manner (in particular in a processor-controlled manner). To this end, the actuating device may have a lug or the like, against which the movable machine element can be pressed so as to actuate the actuating device in a machine-controlled manner. The functional device can therefore be clamped and unclamped by means of a control unit that can be integrated in the main body.

As a movable machine element, the actuating device can comprise a coupling piece for coupling to an electrical actuator device. According to this exemplary embodiment, the actuating device can be actuated automatically by an electronic control system without the need for the intervention of a user. An electrical actuator can be provided for this purpose, which, for example, may function by the servomotor principle.

In such an exemplary embodiment, the apparatus can comprise the electrical actuator apparatus itself. For example, the electrical actuator device can be integrated at least in part or completely in the main body. This electrical actuator device can engage in the coupling piece for transmission of an electrical actuating force to the force transmitting element. In other words, the electrical actuator device can cooperate mechanically with the coupling piece in order to enable the transmission of a force of electrical origin to the actuating element. Such a force then leads directly to a movement of the positioning stops according to a direction and an amplitude of this force.

For example, the electrical actuator device may have a drive shaft and a lever arm disposed thereon. The drive shaft can be equipped to be rotatable and can rotate about its own axis. A transversely projecting lever arm can be provided attached to the drive shaft, and coupling to a force transmitting pin or the like, which can be disposed movably in a linear guide groove of the linear guide device of the actuating element, is possible in the end portion of said lever arm. In this way, the electrical actuating force can be efficiently transmitted. Naturally, a plurality of alternatives to this embodiment are possible.

The positioning stops can be disposed in opposed corner regions of the carrier element. A corner region of the carrier element can be understood in particular as a spatial position at which outer or inner edges of the carrier element abut against one another at an angle, in particular substantially orthogonally (although a certain rounding in such corner regions or along such edges does not need to be excluded). The corresponding component can then be spatially disposed, or is spatially disposable, at or directly adjacent to such a position. According to an exemplary embodiment, a positioning system is provided for the precise positioning of functional device such as, for example, a microtiter plate, wherein the functional device can be supported from a lower side by a main body of the apparatus, can be supported in corner regions by mutually opposed positioning stops of the apparatus, and the positioning stops can be moved manually or automatically by an actuating device such that this can either enable a forceless placement of the functional device on the main body without clamping action of the positioning stops or a non-positive or positive centering of the functional device. In the latter operating state the positioning stops clearly press onto opposed corners of the, for example rectangular functional device from two opposite directions so that this can be positioned two-dimensionally symmetrically in a predefinable manner under the influence of the clamping action. The high positioning accuracy that can be achieved with an apparatus according to an exemplary embodiment of the invention is in particular based on the fact that a central force transmitting element can be disposed in a central portion of the apparatus, in particular in the vicinity of a center of the apparatus, and is in operative communication with the positioning stops disposed for example in opposed corner regions and with the actuating device. The user can thereby undertake an actuator movement at the actuating device in a simple manner, for example a simple sliding movement, which sets in motion a deterministic force transmission mechanism through which the two positioning stops ultimately exert corresponding clamping forces on opposite corners of the functional device. This not only guarantees a highly accurate positioning of the functional device with respect to the apparatus, but also leads to a reliable actuatability. In addition, the system is mechanically stable even when this system is to be operated with the highest precision requirement (for example when the functional device has a plurality of liquid wells in which fluids are to be injected by means of a pipetting robot and/or when a defined shaking movement, for example an orbital movement, is applied to the functional device for mixing the fluidic samples).

Alternatively or in addition, the positioning stops can be disposed at a point other than in opposed corner regions of the carrier element. For example, it is possible for the positioning stops to be disposed at edges (for example in the middle of sides) of the main body so as not to engage corners, but edges (for example the middle of sides) of the functional device in a clamping manner.

The actuating device can be disposed in a (or close to a) corner region of the main body other than that in which the positioning stops are disposed. However, it may be advantageous to dispose the actuating device not in a corner region, but for example on a side edge of the main body, in particular to provide a direction of displacement parallel to a side edge of the main body and/or of the functional device.

The apparatus can be equipped for centering the functional device with respect to a midpoint (or another predefined reference point) of the carrier element. For example, for automatic pipetting requirements it can be desirable to position a functional device in a spatially very precisely defined manner with respect to the apparatus so that a corresponding position signal can be transmitted to the pipetting apparatus, which enables positionally accurate pipetting or the like. According to the exemplary embodiment described, the arrangement of the positioning stops can be designed such that, in the absence of a force applied by a user, the functional device is again and again pushed back into the center of the apparatus. This is accomplished without complex alignment, but can be accomplished merely by force coupling between the at least two positioning stops and the force transmission element as well as the actuating device while simultaneously exerting a predetermined prestress, which can act on the positioning stops.

The apparatus can be designed as a functional device, in particular for positioning a microtiter plate. A microtiter plate can be understood in particular to be a laboratory device for investigating sample properties, for example for an absorption measurement in photometers or for high throughput screening tests in pharmaceutical and plant protection research. Such a microtiter plate may have a rectangular plastics plate, which can also be made of glass or other materials, however. Such a microtiter plate may contain many saucers or wells, which are isolated from one another, in rows and columns. Dimensions of some microtiter plates are standardized. Consequently, a standardized microtiter plate can be centered highly accurately or otherwise positioned in a predefinable manner using the positioning apparatus according to the invention, which substantially simplifies cooperation with further components (automatic pipetting apparatus or photometer arrangement).

The carrier element can be designed as an adapter plate which can be equipped to receive the functional device. The carrier element can thus be specially adapted to a quite specific functional device. For example, a form coding of the carrier element can correspond with a corresponding form coding of the functional device so that an incorrect placement of the functional device on the carrier element is avoided since a positive fit can be avoided in such a case.

The carrier element or the main body may have a temperature-control unit integrated therein for controlling the temperature of a fluidic sample received in the functional device. Such a temperature-control unit can, for example, be an Ohmic temperature control unit, which enables heating of the fluids of the functional device by means of Ohmic losses of an electric current flowing through the carrier element or the main body. Alternatively, such a temperature control may optionally comprise a heating or a cooling, which can be achieved for example by means of a Peltier element. Other temperature-control systems, for example using a cooling or heating medium (for example water) flowing through a cavity in the carrier element or the main body can also be used. By means of such a temperature control, either the temperatures of a sample can be kept constant for example, or alternatively a predetermined temperature cycle can be run through. The latter can be advantageous or desirable for example for PCR ("polymerase chain reaction") analyses. The temperature-control unit can be adjustable in a user-defined manner or can function independently or in a regulated manner. For example, the temperature control unit can be regulated to a certain temperature based on a temperature measured by a temperature sensor.

As a result of the various functions of the carrier element (for example holding, temperature control, other functions are possible), it is possible to exchange the carrier element specially adapted to the needs of an analysis or to mount it on the main body to increase versatility. For example, a set of a plurality of different carrier elements can be used for this purpose, which can all be mounted on the main body.

The positioning stops can be disposed exclusively in two opposed first corner regions of the main body. In other words, according to an exemplary embodiment of the invention, a first corner region of a rectangular carrier element can be provided with a first positioning stop and a diagonally opposed second corner region of the rectangular carrier element can be provided with a second positioning stop. The other two corner regions of the apparatus may then be free from corresponding positioning stops. By using precisely two corresponding and opposed pairs of positioning pieces, both a clamping of corners of the functional device and therefore a secure positioning can be achieved, and also a redundancy of positioning points can be avoided, which may then lead to imprecise positioning of the functional device in the apparatus. Such a configuration is at the same time easy to handle and results in a low weight and small design of the apparatus.

The positioning stops in each respective corner region can be formed by means of two stop elements having mutually perpendicular stop lines for placement against a corner of the functional device. In other words, in any corner region in which a longitudinal edge and an orthogonal transverse edge of the functional device are to be fastened, a first stop element may be provided which applies a force component in a first direction to the functional device. A second stop element that generates a second force component perpendicular to the first direction may further be provided. An inner line (or an inner surface) of the respective stop element is placed against the side wall surface of the functional device, along a line that is straight for example. In functional devices shaped differently, for example round or oval sample containers (for example Petri dishes), the arrangement of the stop elements can be adapted in accordance with the respective geometry.

Alternatively, the positioning stops in a respective corner region can be formed by means of two stop elements having a round cross-section for placement against the functional devices. Such a stop element having a round cross-section can, for example, be a cylindrical pin, in particular a circular cylindrical pin, or a conical pin. A circular cylindrical pin has the advantage of a low cost and can clearly act with a point coupling on a corresponding point of the functional device. Conical pins have the advantage of high versatility and can, for example, taper toward the carrier element on which they can be mounted. A normal force between the carrier element and the functional device can be produced by the tapering of the conical pins toward the carrier element. Adaptation to functional devices of different size is also possible.

The positioning pins for clamping can be equipped to fix microplates having different web heights. In particular, the positioning pins can be formed to support web heights of 2.5 mm, 4.0 mm, and 6.1 mm. For this purpose, the pins can be designed as pins having in particular three O-rings becoming larger toward the top, wherein the O rings act on the upper microtiter plate web edge. It is also possible to design the pins from solid material (for example stainless steel) with corresponding phases and edges. The beveled edges correspond substantially to the function of the O-rings.

Alternatively, the stop elements can be formed as pins having a plurality of rings of different outside diameter mounted thereon. For example, such rings can be made of a flexible material, such as rubber. It is possible that an outside diameter of a respective ring becomes greater, the further away such a ring is located from the carrier element. This enables microtiter plates of different sizes to be inserted into the device.

Alternatively the stop elements can be formed as pins having a plurality of steps of different outside diameter formed integrally thereon. For example, such steps can be fabricated in one-piece or with one material with a core of the pins. It is possible that an outside diameter of a respective step becomes greater, the further away such a step is located from the carrier element. This enables microtiter plates of different sizes to be inserted into the device.

It is also possible to form the positioning stops as pins having a circular cylindrical portion and a conical portion. In particular, a portion mounted on the carrier element can be circular cylindrical and an upper portion adjoining the circular cylindrical portion can be conical. This can lead to a gain in space when handling or lifting out components, such as a plate for example.

The apparatus may further have an electrically controllable pipetting device, which can be equipped for pipetting a fluid into wells of the functional device. For example, a functional device in the form of a microtiter plate having 1536 wells for example can be used. This shows that both the number of wells or saucers and also the demands on the positioning accuracy in such microtiter plates and similar functional devices is very high. A corresponding pipetting robot can control a plurality of pipettes, each of which can pipette in or pipette out a predefined amount of a predefined substance or a substance mixture into an appurtenant well. Even with small positioning inaccuracies, this precise supply or removal of fluids into or from the respective well can be negatively influenced. The positioning device according to the invention can thereby be used particularly advantageously with such an automatic pipetting device. In the case of an electronically controlled actuating device, the electronically controllable pipetting device can be controlled by the same electronic control unit (for example a CPU (central processing unit)) as the electrical actuator device. However, it is also possible for two separate control units to be used.

Alternatively or additionally to a pipetting device, the apparatus may have a shaking device which can be equipped for shaking the sample carrier mounted on the main body. While carrying out a biochemical experiment, it can be necessary or desirable for one or more components or substances to be poured into a respective well of the functional device and mixed with one another or kept in mixing motion (for example in order to avoid a phase separation). Such a mixing operation can be achieved by means of a shaking movement. By means of the provision of the positioning stops according to the invention, a centering of the functional device relative to the apparatus can be maintained during or after a shaking movement.

For example, such a shaking apparatus can be implemented as is described in FIG. 24, FIG. 25 and the following figures of WO 2008/135565, in combination with the respective parts of the description. These exemplary embodiments are included in the disclosure of this patent application by means of explicit reference, which allows the configuration of a shaking device.

In particular, according to the invention, the shaking device can be equipped to act upon the functional device with an orbital movement (for the purpose of shaking). It is possible, for example, that one or more compensating weights is/are mounted on a drive shaft, which is eccentric for example, of such a shaking apparatus so that an uncompensated mass of the apparatus can be at least partially compensated during the shaking movement. In particular, two mutually opposed compensating weights can be disposed along the shaft. It is also possible to ensure that various components of the apparatus are held together by means of magnetic elements during the shaking process.

In the apparatus, the force-transmitting element may have a rotatably mounted coupling disk, which can be coupled mechanically to the actuating device and the positioning stops. A coupling disk can be understood in particular to be a flat disk-like arrangement, for example having a circular base and top surface, which can be designed very flat (for example as a force transmitting plate). A rotatably mounted coupling disk is therefore preferred since this enables a flat design and therefore a space-saving constructive form. For example, a circle diameter of this rotatably mounted circular coupling disk can be at least three times, in particular at least five times, more particularly at least ten times, as great as a cylinder height. The actuating device and the positioning stops can be coupled to an upper (or lower) surface of such a coupling disk, which can be mounted rotatably in a central portion about a midpoint.

The coupling rod or the further coupling rods can be coupled in an articulated manner to the rotatably mounted coupling disk and are connected in an articulated manner to the actuating device or to the respective positioning stop by means of its respective linear guide. Such (further) coupling rods can be designed as rigid elongated struts which can have articulated bearings at two end portions. At these bearings such a (further) coupling rod can be disposed rotatably in an articulated manner. An opposed second end portion of such a (further) coupling rod can be mounted in an articulated manner on the rotatably mounted coupling disk.

These (further coupling rods) may be angled and may therefore have a first straight portion and an adjoining second straight portion. An efficient deflection of force and wear-resistant bearing are made possible by means of such an angled arrangement.

The coupling rod and the further coupling rods may be disposed in a coplanar manner for assembly on the coupling disk. In other words, all the coupling rods can be disposed within a common plane, which enables a flat design. Such a configuration can also reduce or minimize forces perpendicular to such a mounting plane, which can reduce the wear of the rotatably mounted elements and the coupling rods.

For example, all coupling rods can be mounted on a planar (for example circular) top surface of the coupling disk. Such a configuration can be easy to mount and, due to selective adjustability of a respective mounting radius of the coupling rod in relation to the rotatably mounted coupling disk, enables an adaptability of the lever arm to an associated task of the respective components. A further degree of freedom for the adjustability of the force transmission characteristic of the apparatus is thereby given.

The prestressing device and the actuating device can also be mounted in a coplanar manner to one another, that is to say in the same plane. This contributes further to the flat design of the apparatus.

According to an exemplary embodiment, the apparatus has a movably, in particular pivotably, mounted coupling rod, by means of which the actuating device is coupled to the force transmitting element, wherein the coupling rod has a length adjustment mechanism to adjust a length of the coupling rod (which defines a distance between the actuating device and the force transmitting element). Since a length adjustment mechanism is provided, the arrangement can be variably adjusted by a user (or at the factory) to the respective requirements. In particular, it is thus possible to compensate for tolerances of individual component parts, for example the functional device.

According to an exemplary embodiment, the length adjustment mechanism is formed by a first coupling rod part and by a second coupling rod part (at least a third coupling rod part may optionally be provided), wherein the first coupling rod part and the second coupling rod part can be fastened to one another with an adjustable overlap to adjust the length of the coupling rod. The two coupling rod parts may be rigid structures, which are displaceable along one another, wherein a slot in one of the coupling rod parts can be overlapped with a screw hole in the other coupling rod part and one or more fixing screws (possibly with use of a nut or the like) or other fastening elements can be introduced into the overlapping coupling rod parts and fastened so as to fasten said coupling rod parts to one another. To change the length, a user merely has to release the fastening element and set another degree of overlap.

According to an exemplary embodiment, the apparatus has a movably, in particular pivotably, mounted coupling rod, by means of which the actuating device is coupled to the force transmitting element and which contains a first magnet that can be entrained. A second magnet is attached to the carrier element or to the main body and, together with the first magnet, generates an attracting force (in other words the magnets are designed so that they mutually attract one another). The first magnet and the second magnet are disposed in such a manner that, in the operating state engaging the functional device, any distance between the first magnet and the second magnet is less than in the operating state releasing the functional device. With a small distance, the magnets can be disposed parallel to one another (see FIG. 12), and with a larger distance the magnets can be disposed at an angle to one another (see FIG. 13). In other words, the first magnet can be fastened rigidly to the coupling rod, wherein the second magnet can be fastened rigidly to the carrier element or main body. During a transfer of the apparatus between the two operating states, the coupling rod moves (in particular turns), whereby the central or effective distance (based on the strength of the attracting force) between the magnets and therefore the magnitude of the attracting force also changes. The force is greater in the operating state engaging the functional device and therefore holds the coupling rod and consequently the actuating device in the closed state.

At least some of the magnets may be formed as permanent magnets and/or at least some of the magnets may be formed as electromagnets.

According to an exemplary embodiment, in the operating state engaging the functional device, the first magnet and the second magnet can exert the attracting force in a direction substantially parallel to a direction of displacement of the actuating device. The force may have a direction that is opposite an undesired direction of movement of the actuating device and may thus prevent such an undesired movement.

According to an exemplary embodiment, in the operating state engaging the functional device, the first magnet and the second magnet exert the attracting force in a direction substantially perpendicular to a direction of extension of the coupling rod. This promotes the substantially perpendicular alignment of the coupling rod and the direction of displacement of the actuating device.

An exemplary embodiment of the invention connects an orbital mixing by means of magnetic guidance to a central clamping of a microplate. An advantageous aspect is that the central clamping can be combined in conjunction with the shaking/mixing. During shaking, the microplate should be clamped automatically in a central manner in order to reliably hold the microtiter plate, in particular for high mixing speeds or shaking speeds, since the microtiter plate could otherwise be undesirably detached from the apparatus. The shaker itself always stops in its zero position, wherein the central clamping aligns the microtiter plate so precisely that highly precise pipetting into the wells is made possible. Particularly in the case of 384- or 1536-well microtiter plates and increasingly smaller well diameters, this is an important requirement for automatic pipetting. The automatic opening allows both the clamping and also the release of the plate for an exchange of the microtiter plate taking place automatically by robot gripper.

Exemplary embodiments of the present invention will be described in detail hereinafter with reference to the following figures, in which.

Figure 4:
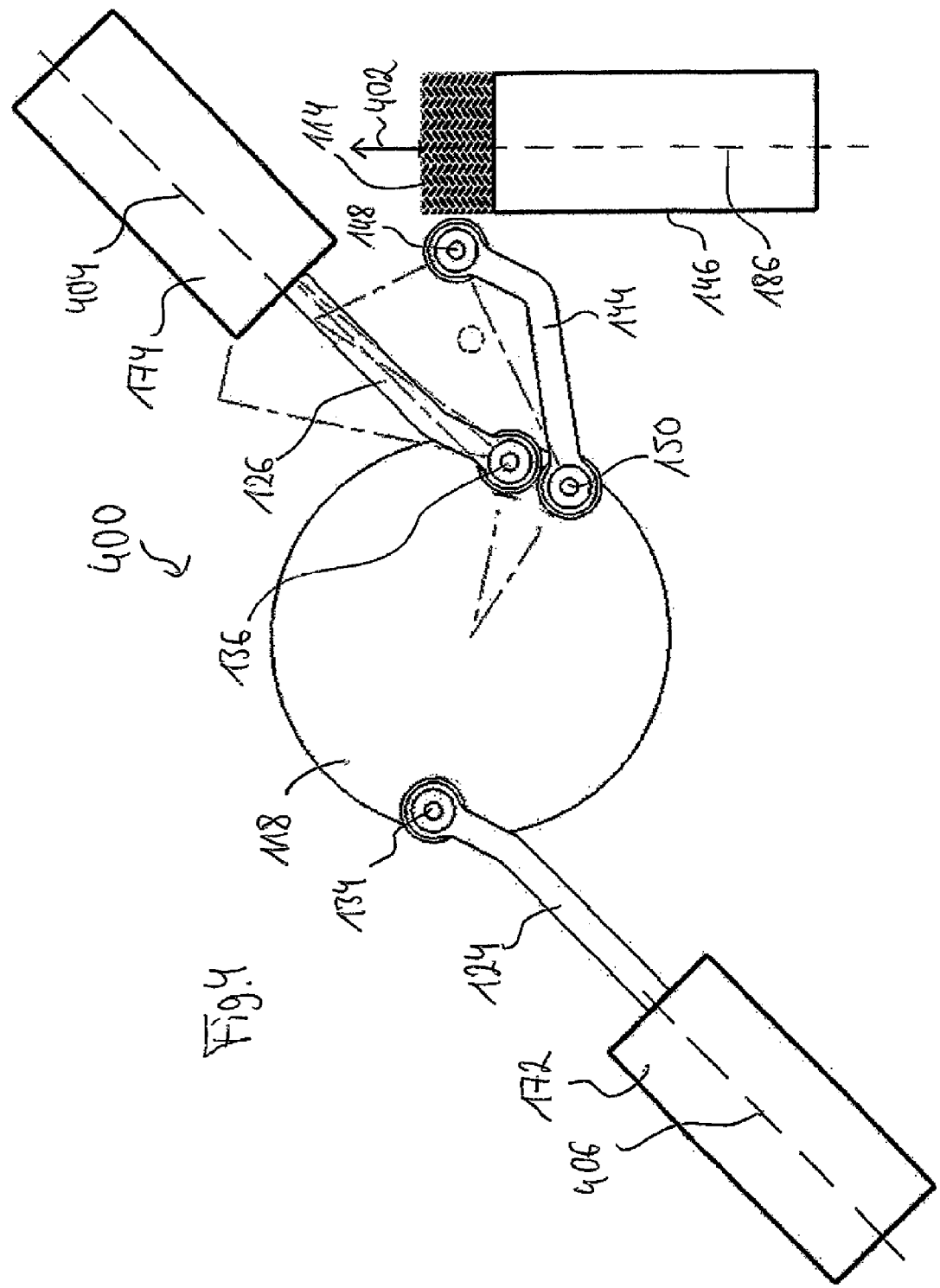
Figure 5:
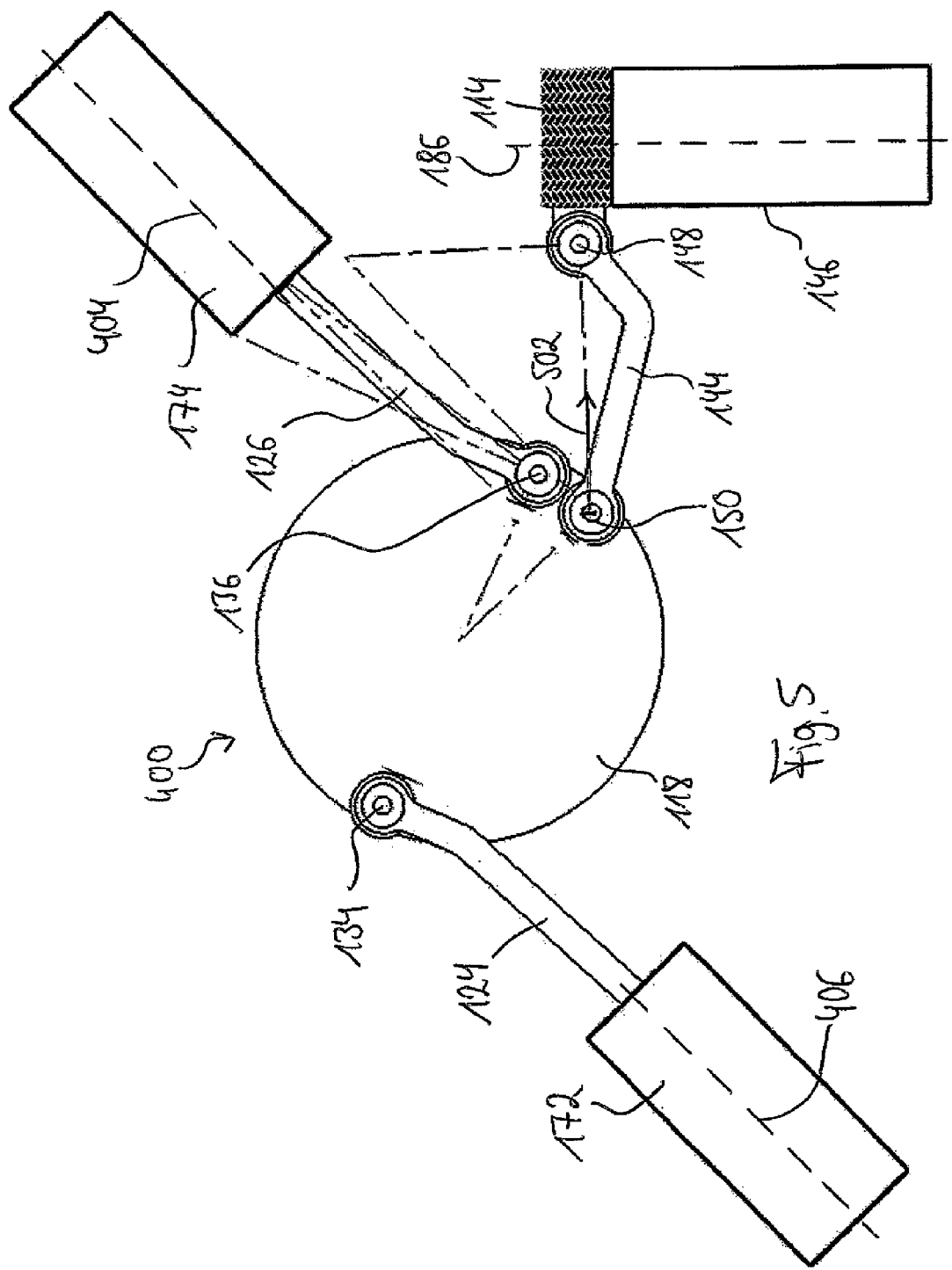

FIGS. 4 and 5 show in plan view schematic diagrams of a positioning device according to one exemplary embodiment of the invention, wherein, in an operating state shown in FIG. 4, a sample carrier plate can be clamped between positioning stops by actuating an actuating device, and wherein, in an operating state shown in FIG. 5, the sample carrier plate is shaken, clamped between positioning stops, without the shaking force undesirably setting the actuating device in motion.

Figure 6:
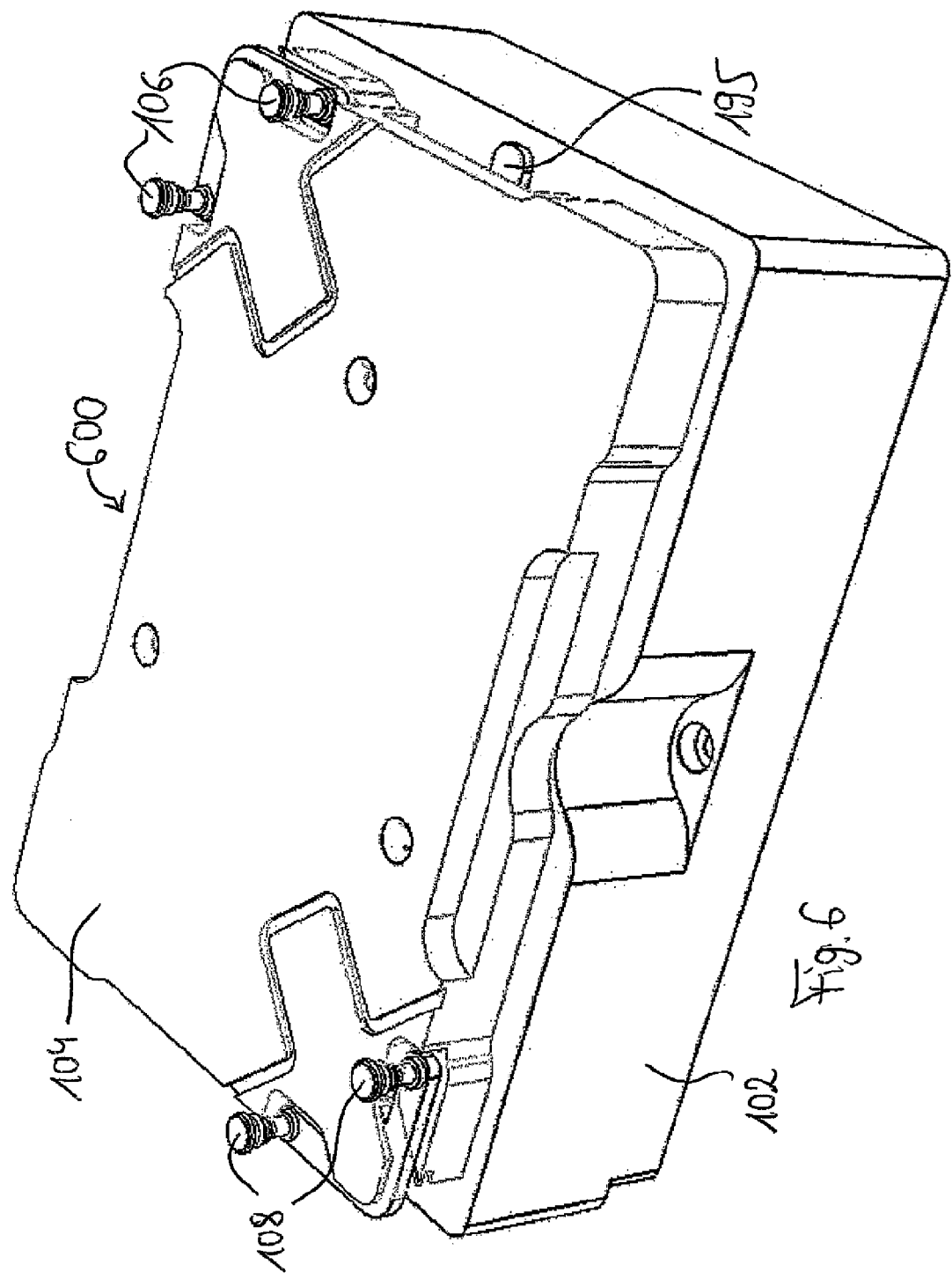

FIG. 6 shows a spatial view of a positioning device according to an exemplary embodiment of the invention in an operating state in which a sample carrier plate still is not placed on a carrier element of the positioning device.

Figure 7:
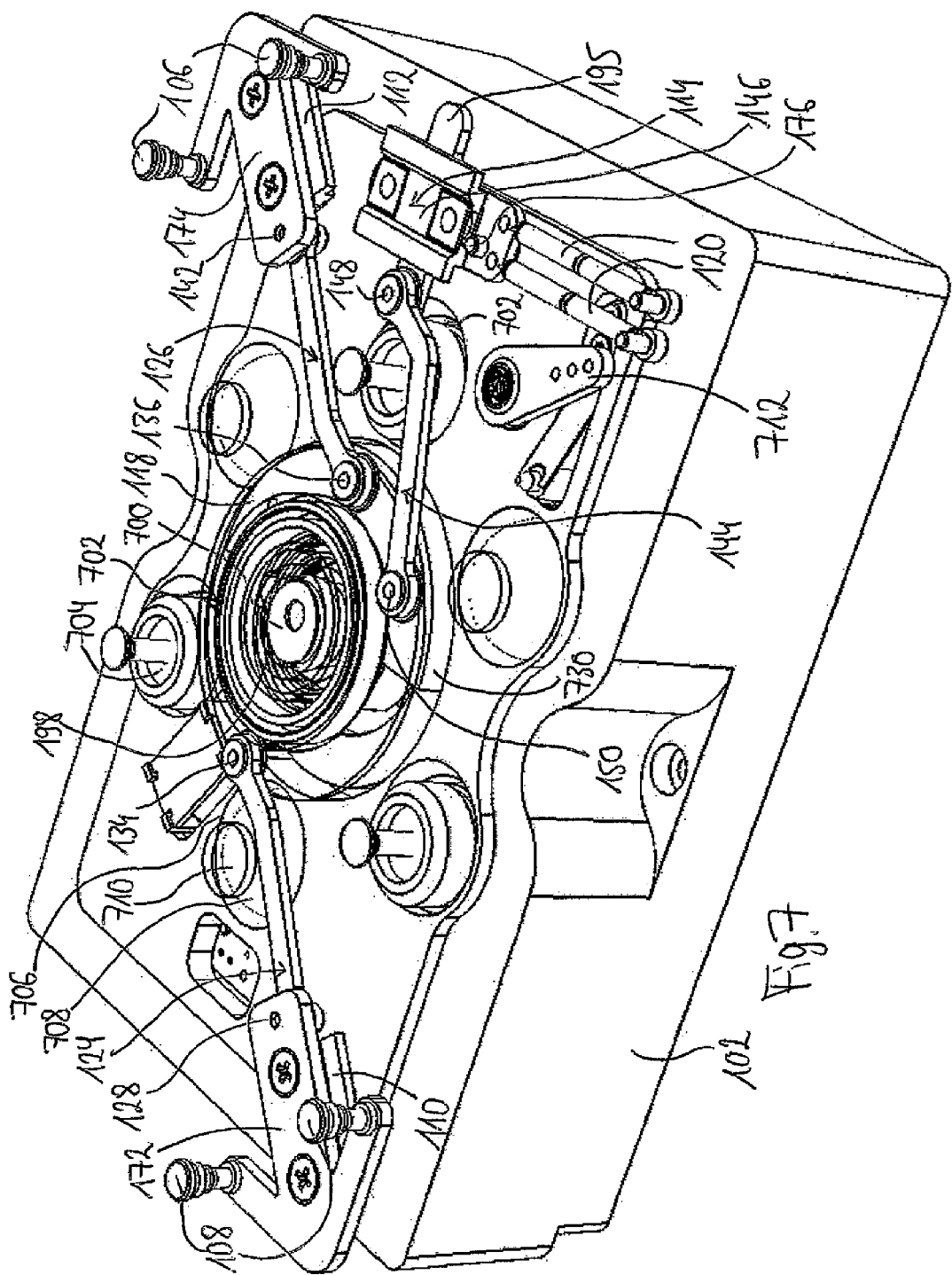

FIG. 7 shows the positioning device from FIG. 6 once a carrier element has been removed, but with some components which are fastened to the carrier element in the assembled state.

Figure 8:
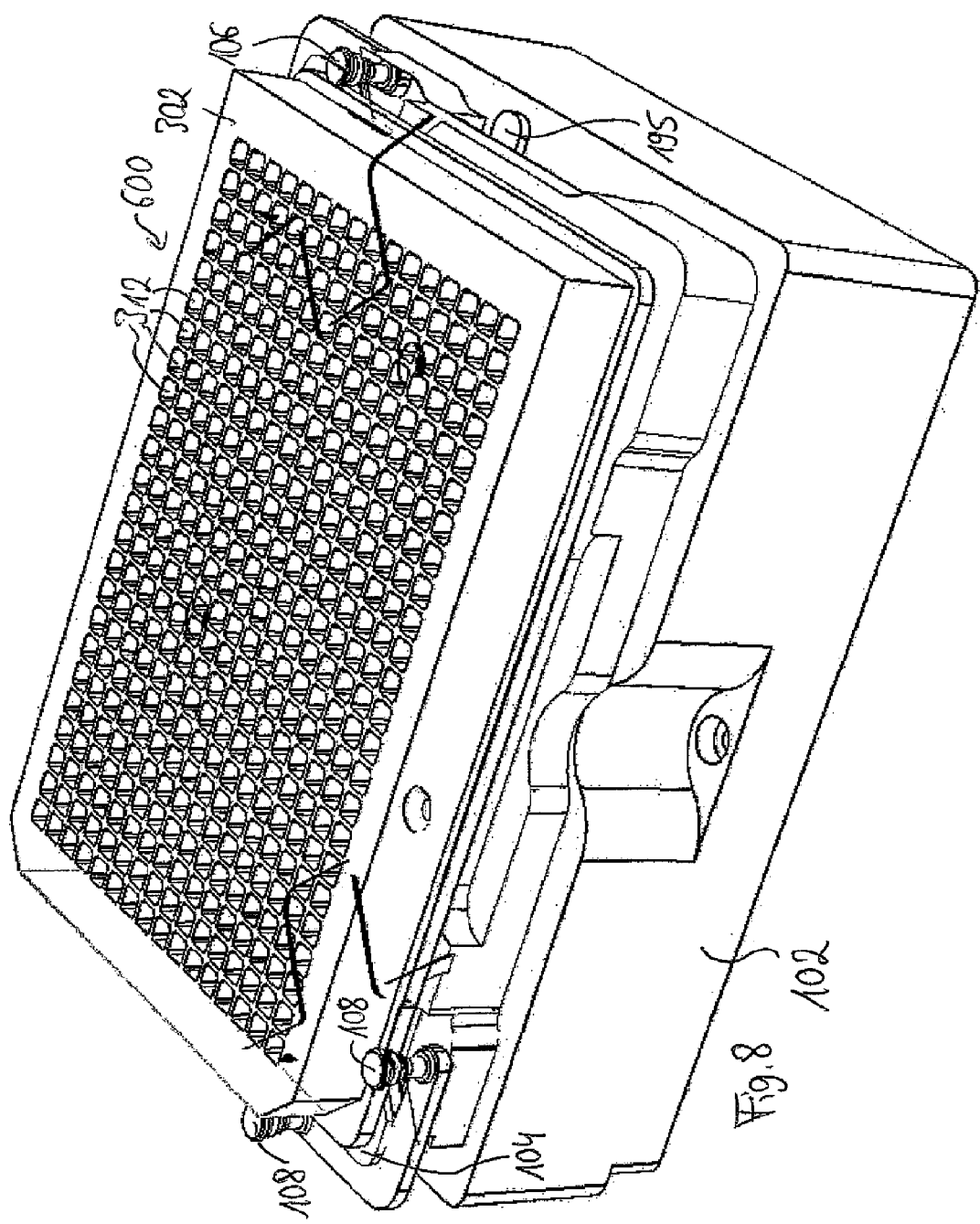

FIG. 8 shows the positioning device from FIG. 6 and FIG. 7 in another operating state, in which the sample carrier plate is engaged by the positioning corners.

Figure 9:
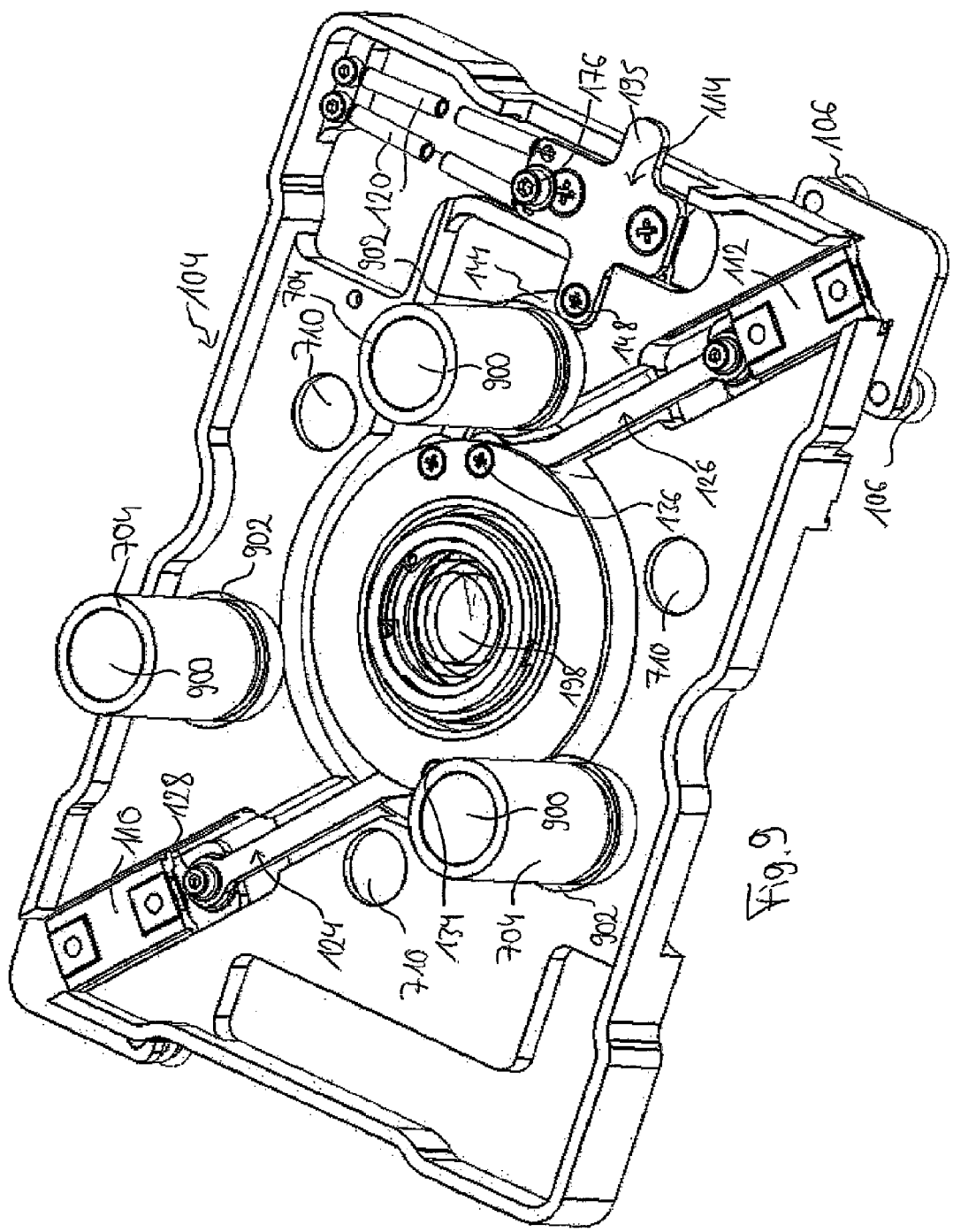

FIG. 9 shows a spatial view from below of a carrier plate, removed from a main body, of a positioning device according to an exemplary embodiment of the invention.

Figure 10:
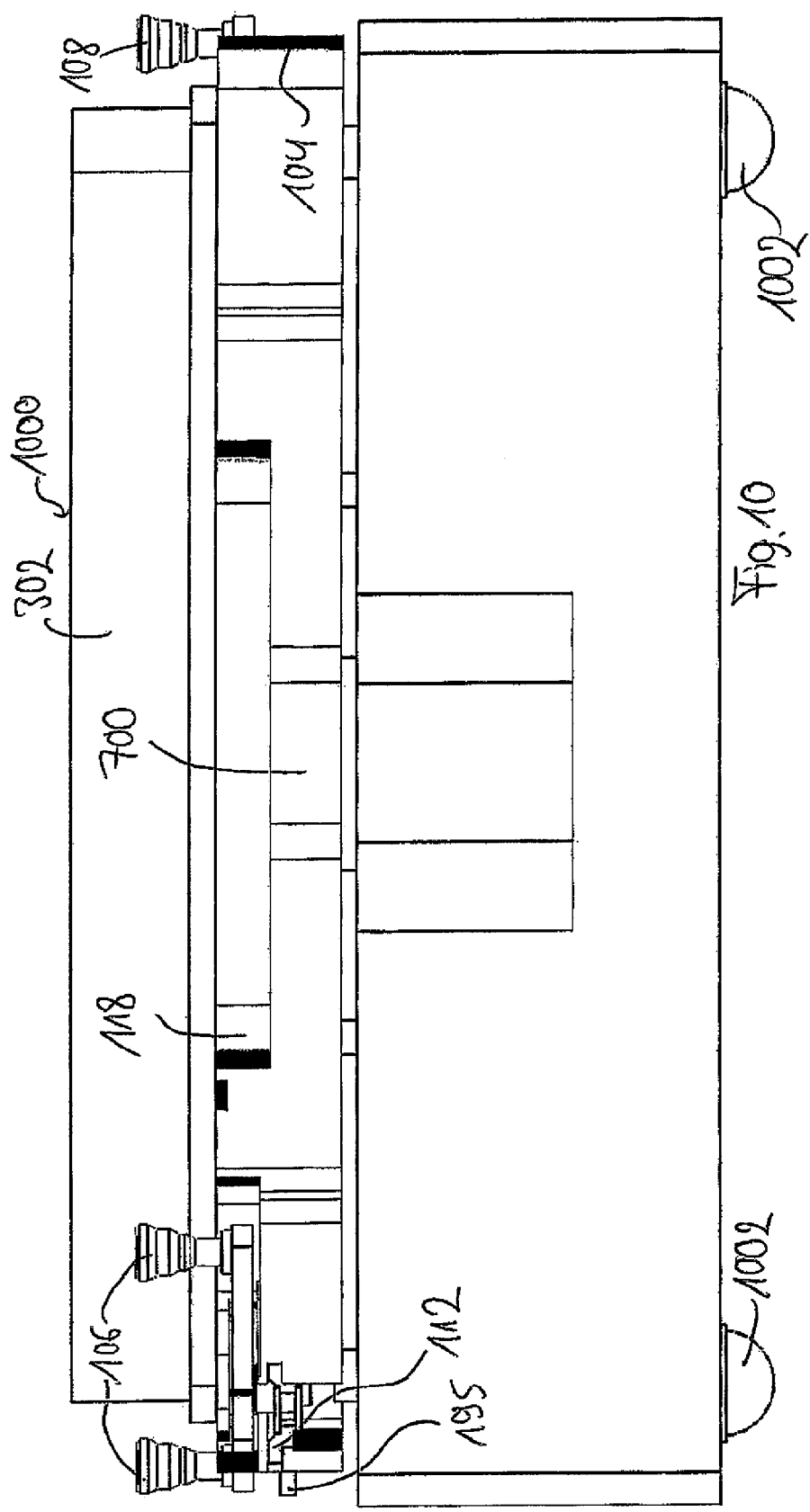

FIG. 10 shows a cross-sectional view of a positioning device according to an exemplary embodiment of the invention.

Figure 11:
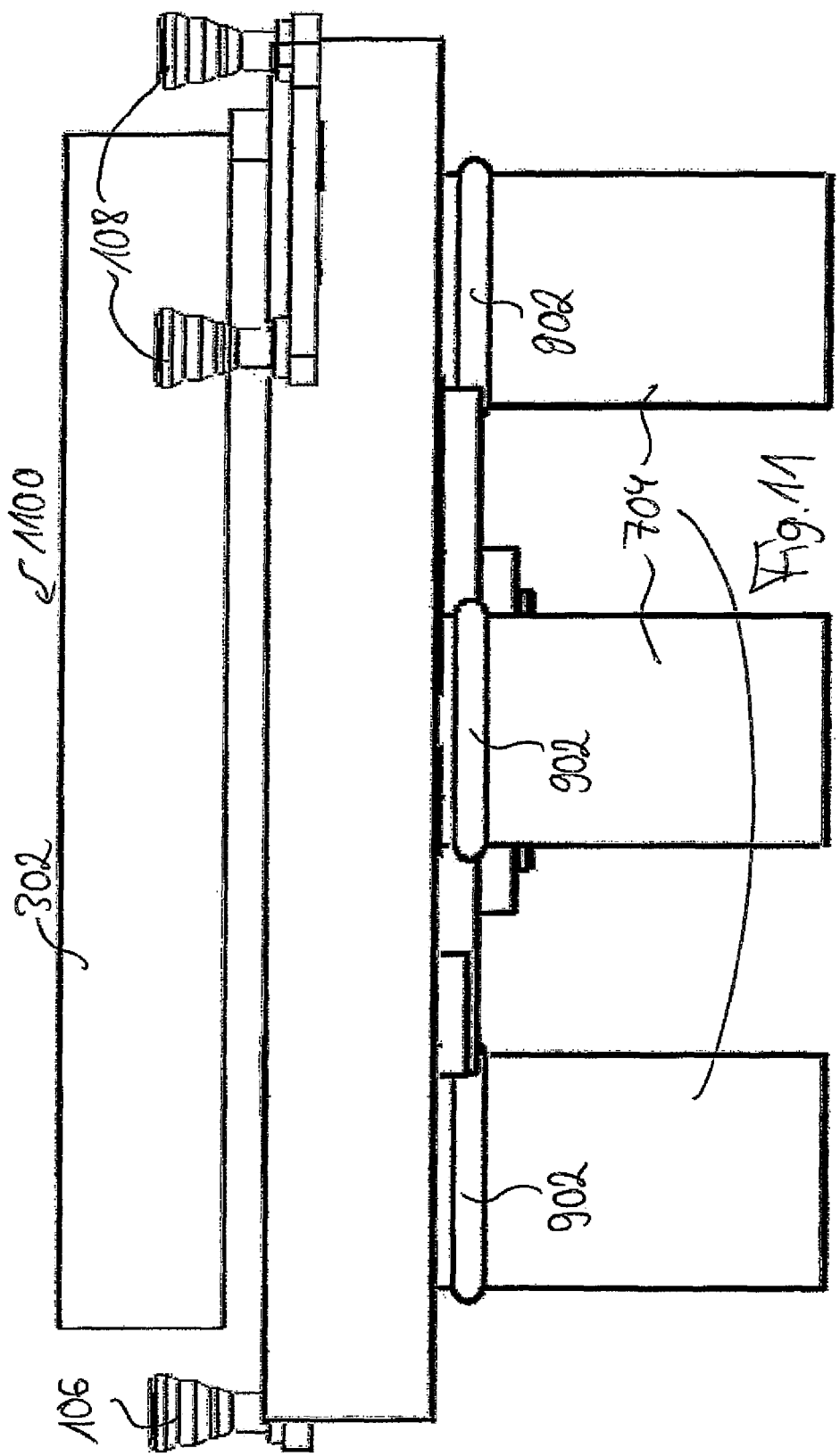

FIG. 11 shows another cross-sectional view of a carrier plate, removed from a main body, of a positioning device according to an exemplary embodiment of the invention.

FIG. 12 shows a plan view of a positioning device according to another exemplary embodiment of the invention in an operating state in which a sample carrier plate (not shown) is released and a carrier element (not shown) is removed from an upper side of the positioning device.

FIG. 13 shows the positioning device from FIG. 12 in another operating state, in which the sample carrier plate (not shown) is engaged by the positioning corners and the carrier element (not shown) is again removed from the upper side of the positioning device.

Like or similar components in different figures are provided with like reference signs.

Exemplary embodiments will be described hereinafter, in which, as a functional device, a sample carrier plate is received in a positioning device. Of course, any other functional device may be received in the respective positioning device in any of these exemplary embodiments.

A sample handling device 100 according to an exemplary embodiment of the invention will be described hereinafter with reference to FIG. 1 and FIG. 2.

Figure 1:
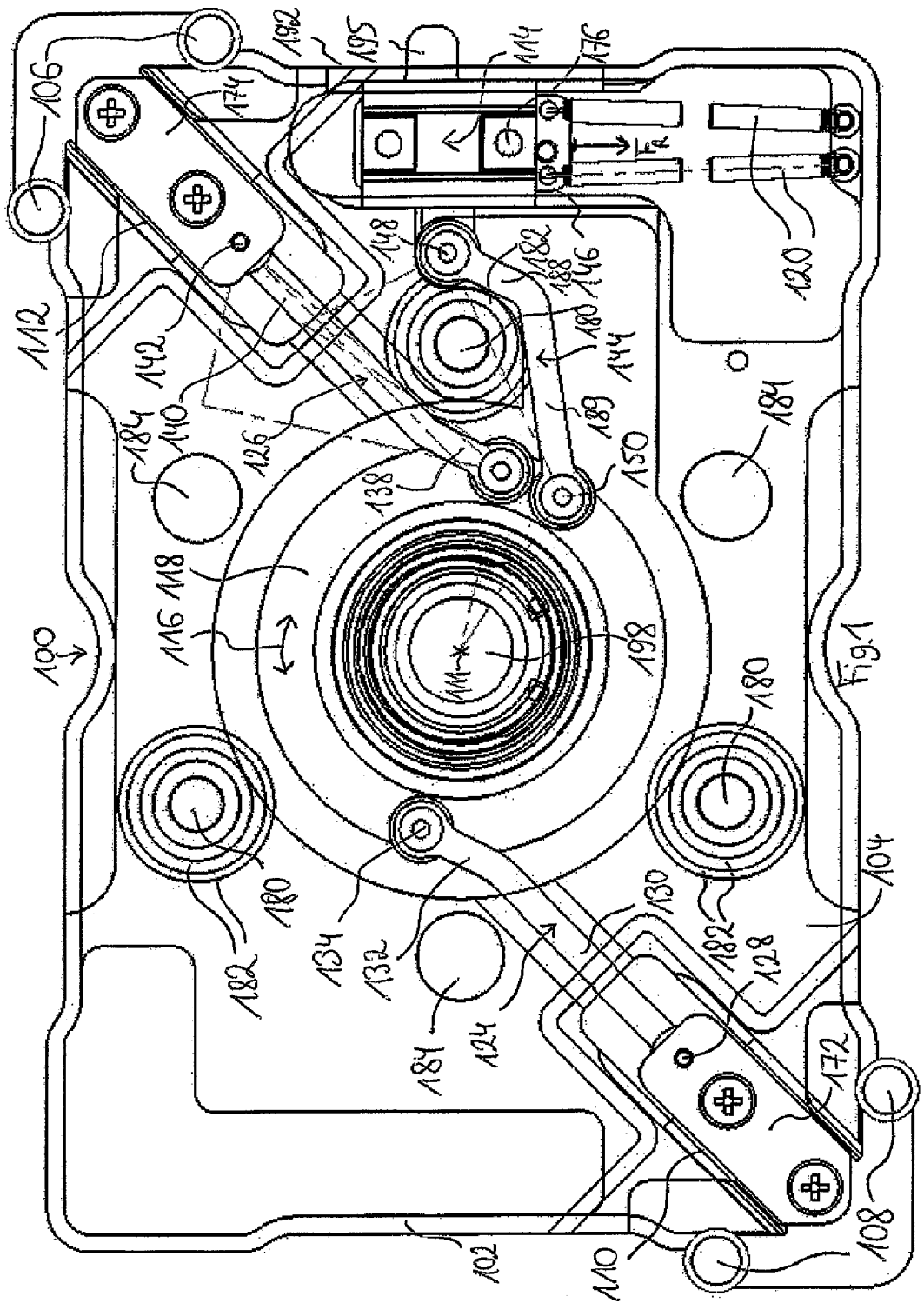
FIG. 1 shows a plan view of a positioning device according to an exemplary embodiment of the invention in an operating state in which a sample carrier plate (not shown) and a carrier element (not shown) are removed from an upper side of the positioning device.
Figure 2:
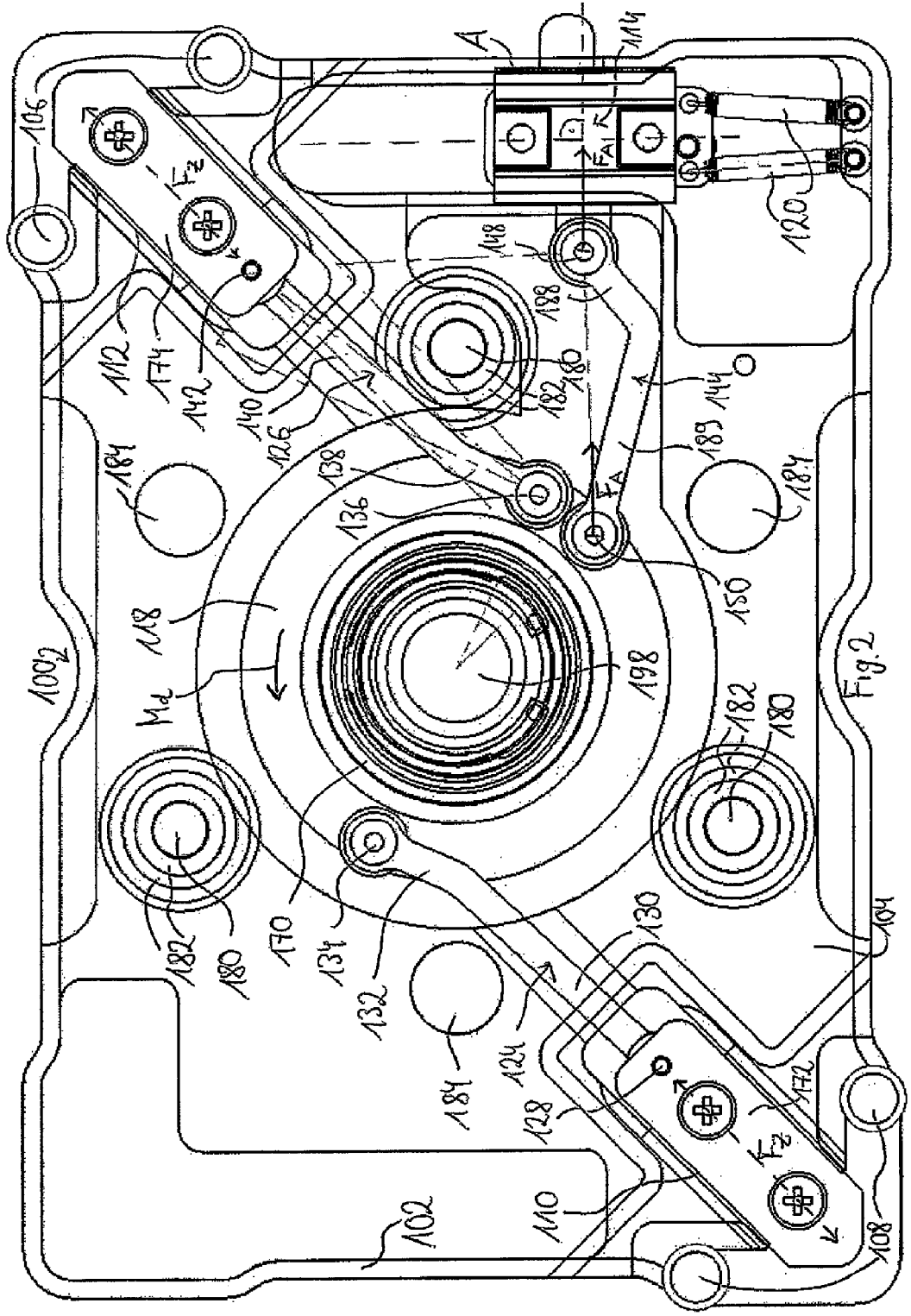
FIG. 2 shows the positioning device from FIG. 1 in another operating state in which the sample carrier plate (not shown) is engaged by the positioning corners and the carrier element (not shown) is again removed from the upper side of the positioning device.

For improved recognition of the individual components, a carrier plate 104 is illustrated transparently in FIG. 1 and FIG. 2. The carrier plate 104 can be seen in detail for example in FIG. 3 and FIG. 6.

The sample handling device 100 contains a substantially rectangular main body 102 shown in plan view, having four substantially right-angled corner regions. On the main body 102, a plate-like carrier element 104 is provided, on which a plurality of different components of the sample handling device 100 are accommodated. The carrier element 104 can be removed from the main body 102, together with these components.

The main body 102 and carrier element 104 can be formed alternatively as a common integral component, but are formed as separable components according to FIG. 1. The main body 102 can have a fixed main housing, and the carrier 104 can be mounted movably on the main body 102.

Two first and cooperating positioning stops 108, designed as pins, are disposed in an upper left corner region of the carrier element 104 according to FIG. 1. Two cooperating pins in the form of positioning stops 106 are mounted in an opposite corner region of the carrier element 104. As is explained in detail hereinafter, the positioning stops 106, 108 are used to clamp a sample carrier plate not shown in FIG. 1, such as a microtiter plate for example.

The positioning stops 108 are functionally operatively coupled to a linear guide device 110. In other words, under the action of a corresponding force on the first positioning stops 108, these are displaced in the direction of a center 111 of the sample handling device 100, whereby the positioning stops 108 slide in a slot-like groove of the linear guide device 110.

Accordingly, the positioning stops 106 can slide in an associated linear guide device 112 so that these can either be displaced jointly with the positioning stops 108 in the direction of the center 111 or slide jointly with the first positioning stops 108 away from the center 111 toward the corresponding corners of the carrier element 104.

An actuating device 114 is accommodated in a lateral edge region of the carrier element 104, disposed between adjacent corner regions, and can be actuated manually by a human user in the exemplary embodiment according to FIG. 1 by sliding a slider or actuator 195 parallel to a side edge 192 (upwardly in accordance with FIG. 1), thus displacing the actuating device 114 in the longitudinal direction with respect to the main body 102. Alternatively, the drive can be produced with use of an electric actuator device. In such an exemplary embodiment, a movable machine element (not shown in FIG. 1), for example a servo lever (see reference sign 712 in FIG. 7) can press against a vertically aligned (from the drawing plane of FIG. 1) pin 176 so as to actuate the actuating device 114.

By means of actuating the actuating device 114 by longitudinally displacing an actuator 195 actuatable by a user or a machine, the positioning stops 106, 108 can each be transferred jointly between an operating state engaging the sample carrier plate and an operating state releasing the sample carrier plate, that is to say not engaging this plate. FIG. 1 shows the released operating state, in which the positioning stops 106, 108 are pushed far into the corner region of the carrier element 104. FIG. 2 on the other hand shows the engaging operating state, in which the positioning stops 106, 108 are disposed closer to the center 111 of the carrier 104 than according to FIG. 1.

As can be identified from FIG. 1, the released operating state corresponds to a position of the actuating device 114 closer in relation to the positioning stops 106 than the engaging operating state according to FIG. 2.

A circular disk 118 mounted rotatably about the center 111, that is to say capable of rotation (see reference sign 116), is provided as a force transmitting element which transfers an actuating force from the actuating device 114 to the positioning stops 106, 108 in such a manner that a displacement of the position of the actuating element 114 from the position shown in FIG. 1 into the position shown in FIG. 2 may necessarily cause a displacement of the positioning elements 106, 108 inward (that is to say in the direction of the center 111) or outward (that is to say away from the center 111). FIG. 1 suggests that the carrier element 104 is coupled to the rotatably mounted coupling disk 118 via a bearing 170.

With the sample handling device 100, it is thus possible for a microtiter plate having a substantially rectangular cross-section to be placed on the central portion of the carrier element 104 and to directly adjoin, in a clamped manner, the positioning stops 106, 108 in two opposite corner regions when the system is in the closed state according to FIG. 2. In the open state according to FIG. 1, a distance remains between the positioning stops 106, 108 and the microtiter plate.

The force transmission mechanism described is thus used to center the microtiter plate in relation to the midpoint 111 of the carrier 104 or a fixed point of the main body 102. This results from the symmetrical fixing of the positioning stops 106, 108 with respect to the circular disk 118 located with its center of gravity in the center 111.

As in each of the exemplary embodiments disclosed here, in the sample handling device 100 shown in FIG. 1, an optional shaking device can also be integrated in the main body 102 and/or in the carrier element 104 (not shown), which can be configured in such a manner that the microtiter plate executes an orbital movement upon reception between the positioning stops 106, 108, and fluids contained in wells of a microtiter plate (for example a liquid and/or a gas, wherein solid components are also not excluded) can consequently be reliably mixed. The clamping action of the positioning stops 106, 108 in the closed position according to FIG. 2 can hold the microtiter plate securely and centered, when averaged over time, with respect to the center 111, even during such an orbital movement.

The force transmission mechanism described cooperates with an arrangement of helical springs 120 serving as a stressing device, which connects a corner region of the carrier element 104 to the actuating device 114 (see FIG. 1 and FIG. 2). A corner region (disposed in the upper left corner in FIG. 1) of the rectangular carrier 104 is completely free of functional elements, but can be equipped, however, with any desired functional elements in other exemplary embodiments. The helical springs 120 can be stressed in such a manner that they transmit a tensile prestress to the rotatably mounted coupling disk 118. One end of each spring 120 is fastened to the carrier 104, wherein the other end of the spring is coupled to the actuating device 114. FIG. 2 shows a basic position of the sample handling device 100, that is to say a state in which a user or an electric control does not exert any mechanical load onto the sample handling device 100. FIG. 1 shows a deflected position of the sample handling device 100, that is to say a state in which a user or an electric control exerts a force deflecting the actuating device by means of a mechanical load on the sample handling device 100. Whilst the helical springs 120 in the basic position are unstressed, the helical screws 120 in the deflected state according to FIG. 1 exert a restoring force $F_R$ onto the actuating device 114.

The sample handling device 100 comprises angled coupling rods 124 and 126. The angled coupling rod 124 couples the positioning stops 108 to the coupling disk 118. In so doing, a connecting element 128 effects an articulated connection between the linear guide device 110 and a first straight portion 130 of the angled coupling rod 124. A second straight portion 132 of the coupling rod 124 is connected in an articulated manner via a connecting element 134 to the coupling disk 118. The angled coupling rod 126 couples the positioning stops 106 to the coupling disk 118. In this case, a connection element 142 provides an articulated connection between the linear guide device 112 and a first straight portion 140 of the angled coupling rod 126. A second straight portion 138 of the coupling rod 126 is connected in an articulated manner to the coupling disk 118 via a connection element 136.

An angled coupling rod 144 formed of a first straight portion 188 and a second straight portion 189 connects the actuating device 114, or a linear guide device 146 of the actuating device 114, to the rotatably mounted coupling disk 118. To this end, the coupling rod 144 contains a connection element 148 for the articulated connection of the coupling rod 144 to the linear guide device 146. A connection element 150 connects the coupling rod 144 to the coupling disk 118 in an articulated manner.

The coupling rods 124, 126 are connected at one end to the coupling disk 118 in an articulated manner. At the respective other end, the coupling rods 124, 126 are connected to linearly guided sliders 172 and 174 respectively in an articulated manner. The positioning stops 106, 108 formed as positioning pins are mounted on each of the two sliders 172, 174. The actuating device 114 is also designed as such a slider.

In the exemplary embodiment according to FIG. 1, the coupling rods 124, 126 and 144 are formed as thin but rigid, metal strips, which are all disposed in the same plane, namely on an upper circular top surface of the thin disk-shaped metal body, which forms a coupling surface of the coupling disk 118. A very space-saving flat design is thus made possible.

An orbital shaking movement can be produced by an eccentrically fixed shaft, which is not shown in FIG. 1 and which is integrated in the main carrier 102. An axis of rotation, about which the eccentrically fixed shaft rotates, is thus offset with respect to a center of mass or a center or gravity of this shaft. This shaft may be provided in an upper end region with a rubber ring and can engage in a central opening 198 inside the coupling disk 118 via said end region. An orbital movement can thus be transmitted to the coupling disk 118 and ultimately to the carrier element 104 with the clamped microtiter plate, whereby the orbital shaking movement is generated.

During such an orbital shaking movement (produced by a shaking device (not shown) integrated into the main carrier 102), which is implemented in the closed state of the mechanism, a centrifugal force acts on the microtiter plate, of which the direction of action is effective in a rotary direction (see reference sign $M_d$ in FIG. 2). However, since the positioning stops 106, 108 are guided linearly over the sliders 172, 174, there is only one possible degree of freedom of the movement due to the centrifugal force $F_z$, which is illustrated in FIG. 2 (closed state) by the indicated arrows. The centrifugal force generates the schematically illustrated torque $M_d$ with respect to the coupling disk 118, from which a force $F_A$ acting on the coupling rod 144 results. The torque $M_d$ and the force $F_A$ are maximal when the rotary direction of action of the centrifugal force and the possible direction of movement of the linear guides of the sliders 172, 174 match.

As illustrated in FIG. 2 however, the force $F_A$, which is transmitted via a coupling rod 144 to the slider 176, acts against a surface A in the closed position of the mechanism perpendicular to the possible direction of movement of the linear guide (caused by the linear guide device 146). Since the actuating device 114 designed as a slider cannot move in this direction, however, the mechanism remains closed and blocked, even if the centrifugal force increases. It is advantageous that a small force at the actuating device 114 designed as a slider is sufficient to move the slider 172, 174, but, conversely in the closed state, the actuating device 114 designed as a slider cannot be moved as a result of the effect of a force at the sliders 172, 174.

In other words, the actuating device 116 and the coupling disk 118 are coupled in such a manner that, in the operating state engaging the sample carrier plate according to FIG. 2, the coupling disk 118 transmits a shaking force of the sample carrier plate to the actuating device 114 in such a manner that the actuating device 114 remains in a rest position with respect to the carrier element 104, in spite of the action of the transmitted sample carrier plate force. This is made possible in particular by the coupling-in of the shaking force $F_A$ perpendicular in relation to a direction of linear displacement 186 of the linear guide device 146.

A direction of extension of the coupling rod 124 may be parallel or substantially parallel (in particular in an angular range of ±20°) to a direction of linear displacement of the slider 172 in the linear guide device 110. A direction of extension of the coupling rod 126 may be parallel or substantially parallel (in particular in an angular range of ±20°) to a direction of linear displacement of the slider 174 in the linear guide device 112. This results in the fact that the coupling rods 124, 126 can efficiently couple in forces onto the positioning stops 106, 108. By contrast, a direction of extension of the coupling rod 144 may be perpendicular or substantially perpendicular (in particular in an angular range of ±20° from a right angle) to the direction of linear displacement 186 of the actuating device 114 formed as a slider in the linear guide device 146. This advantageously results in the fact that the coupling rod 144 cannot couple in forces onto the actuating device 144 so that said actuating device would be noticeably moved.

Regions of balls 180 on the upper side form the only contact points of the carrier element 104, in particular in the vertical or z-direction. The balls 180 are received in spherical receiving openings 182 in the main carrier 102 and protrude slightly therefrom.

The connection force between the balls 180 and the carrier element 104 is produced on the one hand by the force of gravity, which presses the carrier element 104 onto the balls 180. On the other hand, an attracting magnetic force is effective, said force being formed between bolts 184 of the carrier plate 104 having magnet elements and corresponding bolt receiving openings in the main carrier 102, in which magnet elements are likewise incorporated. The magnet elements at the ends of the bolts 184 and in the base regions of the bolt receiving openings in the main carrier 102 attract one another. The carrier element 102 can thus be fixed on the main carrier 104 without screws or the like, and merely by the attracting force of the magnet elements and the force of gravity. Even in a shaking operating state of the sample handling device 100, a connection between the carrier element 104 and the main carrier 102 is thus ensured at all times.

The sample handling device 100 makes it possible to achieve an alignment error of less than 50 μm when fitting and removing, that is to say when clamping or unclamping, a sample carrier plate. If the sample handling device 100 is stopped after a shaking movement, the spatial position of the microtiter plate can be defined with an accuracy of better than 50 μm, and therefore a very precise zero position can be achieved. On the whole, if the above errors are counted together, the accuracy of the positioning is better than 0.1 mm, which is significant in particular for cooperation with a pipetting system or a detection device, for example an optical detection device. Further possibilities for detection are possible, for example optical read-out by means of a high-resolution camera guided in a grid-like manner, object lens systems, photodiodes, photomultipliers or the like can also be provided. A pipetting system may contain a matrix-shaped arrangement of ceramic needles, which are to be dipped into individual wells of a microtiter plate. As a result of the increasing miniaturization, there is a risk that an incorrect positioning of a microtiter plate in the sample handling device 100 may lead to breakage of such needles and therefore to significant damage. With the highly accurate positioning according to the exemplary embodiment of the invention, such an undesired damage to pipetting systems can be reliably avoided, rejects can be reduced and the reliability of a biochemical preparation process can be improved.

The system can be used universally as a system for positioning and shaking sample carrier plates. For example, the highly precise positioning of storage containers disposed in a grid-like manner and equipped with disposable pipetting tips or needles or similar aids is also possible. This means that the robot head can receive, for example, 384 pipetting tips, either individually or together, in a highly accurate manner.

Figure 3:
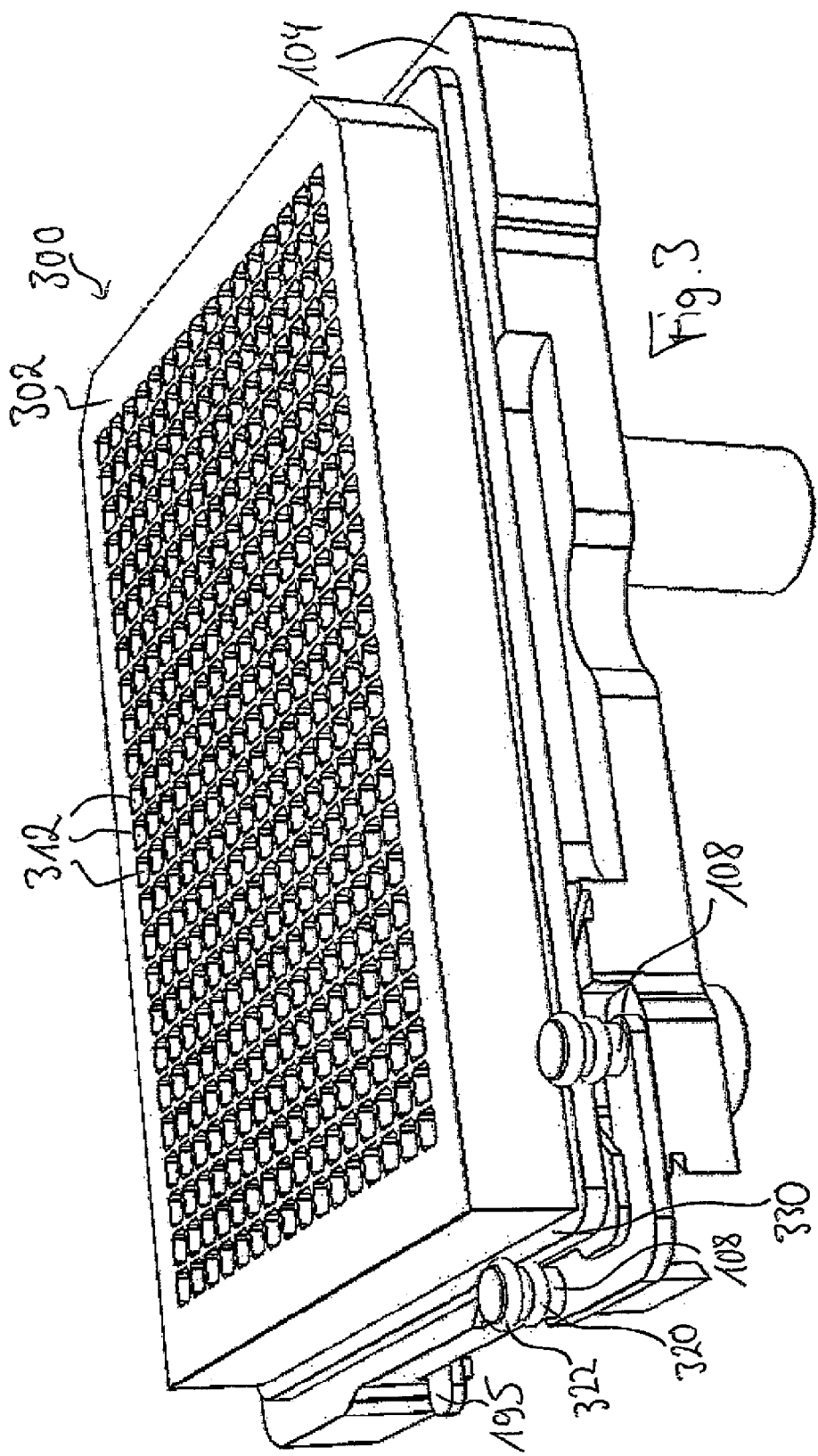
FIG. 3 shows part of a positioning device according to an exemplary embodiment with a mounted microtiter plate.

FIG. 3 shows a three-dimensional view of an arrangement 300 according to an exemplary embodiment of the invention.

The arrangement 300 shows a carrier element 104 with a received microtiter plate 302, but without a main body 102, on which the carrier element 104 can be fitted.

In this exemplary embodiment, the microtiter plate 302 is placed on the carrier 104 and is held laterally fixed. According to the exemplary embodiment of FIG. 3, this is achieved by means of the stop elements 106 and 108 in opposite corner regions of the carrier element 104, which nestle pointwise against side walls of a web 330, that is disposed peripherally on the underside, of the microtiter plate 302. The microtiter plate 302 contains a plurality of wells or sample receiving saucers 312 disposed in a matrix-shaped manner. The microtiter plate 302 can be inserted by a robot arm or manually by a user.

The positioning stops 106, 108 according to FIG. 3 can be formed as conical pins having a plurality of rings 320, 322 of different outside diameter mounted thereon. Any other number of rings is possible. As can be seen most clearly in the left lower region of FIG. 3, a lower ring 320 has a smaller outside diameter than an upper ring 322. Since the rings 320, 322 have different sizes from bottom to top, more specifically increasing sizes in accordance with FIG. 3, microtiter plates of different outside diameters of webs 330 can be clamped in the arrangement 300 in a versatile manner.

FIG. 4 and FIG. 5 show in plan view schematic diagrams of a positioning device 400 according to one exemplary embodiment of the invention. The arrangement can be configured similarly to that shown in FIG. 1, and therefore only the components relevant for explaining the functioning principle of a movement block for preventing any movement of an actuating device 114 as a result of a shaking of a sample carrier plate are shown in FIG. 4 and in FIG. 5.

In an operating state shown in FIG. 4, a sample carrier plate (not shown) is inserted between positioning stops (not shown) by actuating the actuating element 114. If the actuating element 114 is pushed upward in the direction of an arrow 402 according to FIG. 4, the coupling rod 144 is thereby tilted, leading to a turning of the force transmitting disk 118. As a result, the coupling rods 124, 126 are also turned, with the result that sliders 172, 174 are displaced along directions of linear displacement 404, 406 and, consequently, positioning stops are pressed outward.

In an operating state shown in FIG. 5 the sample carrier plate is already clamped between the positioning stops and is shaken by means of a shaking device (not shown) without the shaking force undesirably setting the actuating device 114 in motion. This is accomplished using a force transmission mechanism which is described hereinafter.

The actuating element 114 and the force transmitting disk 118 functioning as force transmitting element are coupled by means of the coupling rod 144 in such a manner that a shaking force of the shaking device is transmitted to the actuating element 114 in such a manner that the actuating element 114 remains in the rest position according to FIG. 5, that is to say it does not move up or down according to FIG. 5, in spite of the action of the transmitted shaking force. The actuating element 114 and the force transmitting disk 118 are coupled by means of the coupling rod 144 in such a manner that, in the operating state according to FIG. 5, the coupling rod 144 couples in the shaking force, see reference number 502, perpendicular to a displacement direction 186 of the actuating element 114.

In an orthogonal position between the coupling rod 144 and the displacement direction 186 according to FIG. 5, no shaking force component can lead to a movement of the actuating device 114, and therefore this type of force transmission advantageously blocks the movement. By contrast, in the other force transmission direction, that is to say from the actuating device 114 to the sliders 172, 174, a force transmission leading to a movement can take place since the coupling rods 124, 126 are not perpendicular (but even approximately parallel) to the directions of linear displacement 404, 406.

In the closed state according to FIG. 5, an angle of almost 90° can be achieved between the coupled-in shaking force 502 and direction of displacement 186. The system is then so well clamped that the springs 120 could also be omitted. It is almost impossible to push the system over the corners, and the system also reliably withstands very high shaking speeds.

A positioning device 600 according to another exemplary embodiment of the invention will be described hereinafter with reference to FIG. 6 to FIG. 8.

In the operating state shown in FIG. 6, the carrier element 104, with the functional components integrated therein, is placed on the main carrier 102.

Similarly to FIG. 1 and FIG. 2, FIG. 7 shows a spatial illustration of the positioning device 600, once the carrier plate 104 has been removed. For improved comprehension of the cooperation of the individual components of the positioning device 600 however, a number of components, which are connected securely to this carrier plate 104, are shown in FIG. 7.

In the positioning device 600, a pair of helical springs 120 is provided, which are disposed parallel to one another between a corner region of the carrier element 104 and a portion of the actuating device 114. In a zero position of the actuating device 114, which corresponds to an operating state engaging a microtiter plate (not shown), the helical springs 120 are in an unstressed state. If, by contrast, the actuating device 114 is displaced in the direction of the positioning stops 106, for example by the muscular force of a user or by an electric force of a robot, a restoring force is exerted due to the provision of the two parallel springs 120 and has a tendency to return the actuating device 114 into the zero position.

The positioning stops 106, 108, the actuating device 114 and the force transmitting element 118 are disposed on the carrier element 104, which is removed in FIG. 7, and are movable jointly with respect to the main carrier 102.

FIG. 7 further shows that an eccentrically mounted shaft 700 is disposed in a main body 102. This shaft engages in the recess 198 in the coupling disk 118. When the eccentric shaft 700 is driven by an electric motor for example, this leads to an orbital movement of the eccentric shaft 700, which leads to an orbital movement of the coupling disk 118. This causes an orbital movement of the carrier plate 104 and of the positioning stops 106, 108.

Three hollow cylindrical recesses 702 are formed in the main body 102 around the coupling disk 118, a respective bolt 704 engaging in said recesses and being screwed at an underside of the carrier plate 104. Permanent magnets are disposed at a lowest point of the recesses 702 and exert an attracting force on corresponding permanent magnets, which are disposed on an underside of the bolts 704 (not shown). An exclusively magnetic fastening between the carrier element 104 and the main carrier 102 is thus implemented. An air gap is formed between the attracting magnets in each case.

In addition, a plurality of spherical seats 706 are formed in the main body 102, into each of which a ball 708 is introduced, said balls protruding upwardly from these spherical seats 706. Plates 710 made of a low-friction material are formed at the underside of the removed carrier element 104. This is understood to mean that, when the balls 708 in the spherical seats 706 move, there is only an extremely small frictional force between the plates 710 and the balls 708. Although this is not shown in FIG. 7, such a plate 710 may likewise be provided at a lowest point in the spherical seats 706 so as to also enable low-friction sliding on an underside of the balls 708. The uppermost points of the balls 708 form the only direct contact points of the carrier element 102 on the main body 102. The disks or plates 710 can be formed from a ceramic material.

A movable (between two or more switch positions) machine element, for example a pivotable servo arm 712, is also shown clearly in FIG. 7 and can be driven by an electric motor, which is integrated for example in the main body 102, and can press selectively against a pin 176 on the actuating element 114 so as to displace it. The positioning device 600 can therefore be mechanically switched between the operating state releasing the sample carrier plate and the operating state engaging the sample carrier plate. Alternatively, the positioning device 600 can be operated by a human user, who thus displaces the actuator lever 195 along a side edge of the positioning device 600.

Alternatively to the servo system, a linear drive, for example a spindle drive or a toothbelt drive, with a slot can be provided, said slot being so large that an actuation engagement point, for example a cylindrical pin of the actuating element, can also be shaken in the event of shaking operation. An actuator movement can also be carried out in this slot.

FIG. 7 also shows a compensating weight 730, which is used to counterbalance forces that can be generated by an eccentric fixing of the eccentric shaft 700. The compensating weight 730 is formed as an approximately semi-hollow cylindrical plate. In addition to the compensating weight 730, a further compensating weight that is not shown in FIG. 7 may be provided, which enables balancing to a finer extent.

FIG. 8 shows the positioning device 600 in an operating state in which a microtiter plate 302 with a plurality of wells 312 is clamped between the opposed positioning stops 106, 108.

In contrast to the positioning stops 106, 108 according to FIG. 3, the positioning stops 106, 108 according to FIG. 8 are formed as stainless steel pins having three steps of different outside diameter formed integrally thereon. These integrally formed steps of different outside diameter perform a function similar to that of the rubber rings 320, 322, 324 of the positioning stops 106, 108 according to FIG. 3, but can be produced particularly advantageously in terms of the manufacturing technology required.

FIG. 9 shows a view from below of the carrier element 104 according to the exemplary embodiment of FIG. 6 to FIG. 8. In FIG. 9, the permanent magnet elements are also shown on the underside of the bolts 704 and are provided with reference sign 900.

Reference sign 902 denotes resonance damping elements in the form of rubber rings, which are fitted over an outer peripheral surface of the bolts 704 and may be fixed there (for example by gluing). In undesirable conditions, it may be that a shaking apparatus with the positioning device 600 comes into the range of a resonance frequency. The entire positioning device 600 then vibrates undesirably at this frequency, which for example may lie at 1500 revolutions/min. This may lead to an undesired movement of the entire apparatus on an underlying surface. To avoid this, the resonance damping elements 902 are provided. They are normally disposed at a distance from the surrounding side walls of the bolt receiving openings 702. If resonance occurs, however, the resonance damping elements 902 are thus pressed against such a side wall, which leads to a damping of this resonance vibration. The system can thus be brought out of resonance.

As shown by the cross-sectional view 1000 shown in FIG. 10 of a positioning device according to an exemplary embodiment of the invention, damping elements 1002 in the form of rubber nubs or the like can be provided on the base of the main carrier 102.

The geometry of the chamfered positioning stops 106, 108, made from one material, and the attachment of the resonance damping elements 902 to the bolts 704 can be seen particularly clearly in a cross-sectional view 1100 according to FIG. 11.

A sample handling device 1200 in accordance with an exemplary embodiment of the invention will be described hereinafter with reference to FIG. 12 and FIG. 13. The operating state of FIG. 12 corresponds to that of FIG. 1, and the operating state of FIG. 13 corresponds to that of FIG. 2. Only the main differences of the sample handling device 1200 compared to the sample handling device 100 will be described hereinafter.

The sample handling device 1200 contains a rigid, pivotably mounted coupling rod 1202, by means of which the actuating device 114 is coupled to the force transmitting element 118. The coupling rod 1202 has a length adjustment mechanism for adjusting a length L (see FIG. 13) of the coupling rod 1202. The length adjustment mechanism is formed by a first coupling rod part 1204 and by a second coupling rod part 1206, wherein the first coupling rod part 1204 and the second coupling rod part 1206 can be fastened to one another with an adjustable overlap B to adjust the length of the coupling rod 1202. L can be varied by varying B.

A first magnet 1208, which can be pivoted in an entrained manner, is fixed on the coupling rod 1202, more precisely on the second coupling rod part 1206. A second magnet 1210 is attached securely to the carrier element 104 and produces an attracting force together with the first magnet 1208 (in other words, the two magnets 1208, 1202 attract one another). The first magnet 1208 and the second magnet 1210 are disposed in such a manner that, in the operating state engaging the functional device according to FIG. 13, a central distance between the first magnet 1208 and the second magnet 1210 is smaller than in the operating state releasing the functional device according to FIG. 12.

According to FIG. 13, the first magnet 1208 and the second magnet 1210 exert the attracting force vertically and therefore in a direction parallel to a direction of displacement of the actuating device 114. At the same time, the first magnet 1208 and the second magnet 1210 exert the attracting force perpendicular to a substantially horizontal direction of extension of the coupling rod 1202 in accordance with FIG. 13.

FIG. 12 therefore shows the locking mechanism in an opened state, with the positioning corners 106, 108 (or pins) extended. By contrast, FIG. 13 shows the locking mechanism in the closed state, with the positioning corners 106, 108 retracted. The magnet pair 1208, 1210 functions in an attracting manner and the coupling rod 1202 is disposed at 90° to the actuating device 114 (slider).

In FIG. 12 and FIG. 13, so as to further improve the action of the mechanism, the coupling rod 1202 is a) split into two and provided with an adjusting element (screw connection) and b) the magnet pair 1208, 1210 is also introduced.

This has the Following Advantages, Inter Alia

According to a), the coupling rod 1202 is split into two. Two threaded bores and two set screws are introduced in the second coupling rod part 1206. The first coupling part 1204 is provided with a narrow slit in the width of the screw thread. Now, as a result of the establishment of the two screws, a1) both coupling rods parts 1204, 1206 can thus be connected to form the rigid coupling rod 1202, and a2) a displacement and adjustment can be carried out. The purpose of the adjustment is to achieve, where possible, an ideal 90° position between the coupling rod 1202 and the displacement element 114 when the pins are retracted (depending on the tolerance-dependent outer dimensions of the sample carrier to be clamped). Conventional sample carriers, generally microtiter plates in ANSI SBS format, are generally subject to tolerances and have different peripheral edge geometries. If the sample carrier is known beforehand for a specific application, an ideal clamping state with a 90° position between the coupling rod 1202 and the displacement element 114 can thus be adjusted and achieved.

With reference to b), the magnet pair 1208, 1210 boosts the positive effect of a) in the closed state. An advantageous effect is the realization of the ideal 90° position, which can never be achieved completely due to the tolerance-dependent outer dimensions of the sample carrier to be used. The magnet pair 1208, 1210, which functions in an attracting manner in the closed state, assists the adoption of the desired 90° positioning. The magnet pair 1208, 1210 also functions extremely advantageously in the event of severe shaking movements, wherein greater forces with a tendency toward an undesired opening act on the pins through the sample carrier, and assist the retention of the practically ideal 90° position.

If the mechanism is then to be opened again, the displacement element 114 is thus to be displaced manually or by a drive, wherein the magnet force then also additionally has to be overcome. With a suitable selection of the magnetic field strength, a good technical compromise can be made. In one exemplary embodiment it is also possible for one or both of the magnets 1208, 1210 to be designed as an electromagnet, so that, by disconnecting an excitation voltage in the engaging state, the then undesired attracting force of the magnets is interrupted or can even be converted into a repelling force.

In addition, it should be noted that "comprising" does not exclude any other elements or steps and "an" or "a" does not exclude a plurality. It should also be noted that features or steps which have been described with reference to one of the above exemplary embodiments can also be used in combination with other features or steps of other exemplary embodiments described above. Reference signs in the claims are not to be considered as limiting.

The invention claimed is:

1. An apparatus for positioning a functional device, wherein the apparatus has:
 a main body;
 a carrier element that can be disposed on the main body to receive the functional device, wherein the functional device is a sample container, a carrier plate or a storage or receiving container disposed in a grid-like manner;
 positioning stops, which are mounted displaceably to clamp the functional device;
 an actuating device which is adapted such that, by actuating the actuating device, the positioning stops can be transferred between an operating state engaging the functional device and an operating state releasing the functional device, wherein a functional device force is exertable by the functional device onto the positioning stops in the operating state engaging the functional device;
 a force transmitting element which is adapted to transmit an actuating force from the actuating device to the positioning stops;
 a coupling rod which is pivotably mounted by a first connecting element to the actuating device and is pivotably mounted by a second connecting element to the force transmitting device; and
 movably mounted further coupling rods, by which the positioning stops are coupled to the force transmitting element, wherein the positioning stops are transferred between the operating state engaging the functional device and the operating state releasing the functional device by pivoting the further coupling rods,
 wherein the positioning stops are transferred between the operating state engaging the functional device and the operating state releasing the functional device by pivoting the coupling rod, and
 wherein the actuating device and the force transmitting element are coupled via the coupling rod in such a manner that, in the operating state engaging the functional device, the force transmitting element transmits the functional device force of the functional device to the actuating device such that the actuating device remains in a rest position with respect to the carrier element, in spite of the action of the transmitted functional device force.

2. The apparatus according to claim 1, having a linear guide device for defining a direction of linear displacement of the actuating device, the actuating device being exclusively displaceable along said direction of linear displacement, wherein, in the operating state engaging the functional device, the coupling rod is oriented such that the functional device force is transmitted to the actuating device in a manner acting perpendicular to the direction of linear displacement.

3. The apparatus according to claim 1, further having:
 further linear guide devices for defining further directions of linear displacement of the positioning stops, the positioning stops being exclusively displaceable along said further directions of linear displacement, wherein the further coupling rods are oriented such that the actuating force is transmitted to the positioning stops in a direction parallel to the further directions of linear displacement.

4. The apparatus according to claim 1, wherein the coupling rod has a first portion extending in a straight line and a second portion extending in a straight line, wherein the first portion extending in a straight line and the second portion extending in a straight line are angled relative to one another.

5. The apparatus according to claim 2, wherein the direction of linear displacement extends parallel to a lateral delimiting edge of the carrier element.

6. The apparatus according to claim 1, wherein the actuating device is disposed at a side region of the carrier element between two adjacent corner regions of the carrier element.

7. The apparatus according to claim 1,
 wherein the force transmitting element has a rotatably mounted coupling disk, which is coupled to the actuating device and to the positioning stops,
 wherein the actuating device is coupled to the rotatably mounted coupling disk by the coupling rod, wherein the coupling rod is connected in an articulated manner by the first connecting element to the rotatably mounted coupling disk and is connected in an articulated manner by the second connecting element to the actuating device by a linear guide, and
 wherein the actuating device and the force transmitting element are coupled by the coupling rod such that, in the operating state engaging the functional device, the coupling rod transmits a shaking force perpendicular to a direction of displacement of the actuating device.

8. The apparatus according to claim 1, having a clamping device disposed between the carrier element and the actuating device, said clamping device being adapted to transmit a tensile clamping force, to the actuating device, wherein the clamping device has a plurality of springs disposed parallel to one another.

9. The apparatus according to claim 8, wherein an end of the clamping device is disposed in a corner region of the carrier element.

10. The apparatus according to claim 1, wherein the positioning stops, the actuating device and the force transmitting element are disposed on the carrier element and are movable jointly with respect to the main body.

11. The apparatus according to claim 1, wherein an eccentrically mounted shaft is disposed on the main body and engages in a recess in the force transmitting element of the carrier element and can be driven to exert an orbital shaking movement of the main body.

12. The apparatus according to claim 1, wherein at least one recess with a magnet element provided therein is formed in the main body, wherein at least one bolt of the carrier element with a magnet element provided thereon can be received in the at least one recess, wherein the main body can be fastened on the carrier element by means of an attracting force between the at least one magnet element of the carrier element and the at least one magnet element of the main body, wherein the at least one bolt has a resonance damping element which presses in the respective recess against the main body in the event of under a resonant shaking movement so as to bring the apparatus out of resonance.

13. The apparatus according to claim 1, wherein a plurality of spherical seats with balls disposed therein are formed in the main body, the carrier element resting against said balls.

14. The apparatus according to claim 1, wherein the positioning stops are disposed exclusively in two opposed corner regions of the carrier element.

15. The apparatus according to claim 1, wherein the positioning stops are formed by means of two stop elements having stop lines perpendicular to one another for placement against a rectangular functional device.

16. The apparatus according to claim 1, wherein the coupling rod and the further coupling rods are disposed in a coplanar manner.

17. The apparatus according to claim 1, having:
a pivotably mounted coupling rod, by means of which the actuating device is coupled to the force transmitting element and which contains a first magnet that can be entrained;
a second magnet, which is mounted on the carrier element or on the main body and, together with the first magnet, generates an attracting force;
wherein the first magnet and the second magnet are disposed such that, in the operating state engaging the functional device, a distance between the first magnet and the second magnet is less than in the operating state releasing the functional device.

18. A method for positioning a functional device, wherein the method has the following steps:
arranging the functional device between positioning stops mounted displaceably on a carrier element in an operating state releasing the functional device to receive the functional device on the carrier element, which is disposed on a main body; wherein the functional device is a sample container, a carrier plate or a storage or receiving container disposed in a grid-like manner;
clamping the functional device between the positioning stops by actuating an actuating device to transfer the positioning stops from the operating state releasing the functional device into an operating state engaging the functional device, wherein a functional device force is exertable by the functional device onto the positioning stops in the operating state engaging the functional device;
transmitting an actuating force from the actuating device to the positioning stops by means of a force transmitting element;
wherein a coupling rod is pivotably mounted by a first connecting element to the actuating device and is pivotably mounted by a second connecting element to the force transmitting device,
wherein further coupling rods are movably mounted, by which the positioning stops are coupled to the force transmitting element, wherein the positioning stops are transferred between the operating state engaging the functional device and the operating state releasing the functional device by pivoting the further coupling rods,
wherein the positioning stops are transferred between the operating state engaging the functional device and the operating state releasing the functional device by pivoting the coupling rod, and
transmitting the functional device force of the functional device from the force transmitting element via the coupling rod to the actuating device in the operating state engaging the functional device, in such a manner that the actuating device remains in a rest position with respect to the carrier element, in spite of the action of the transmitted functional device force.

* * * * *

UNITED STATES PATENT AND TRADEMARK OFFICE
CERTIFICATE OF CORRECTION

| | | |
|---|---|---|
| PATENT NO. | : 9,126,162 B2 | |
| APPLICATION NO. | : 13/635901 | |
| DATED | : September 8, 2015 | |
| INVENTOR(S) | : Olaf Simmat | |

It is certified that error appears in the above-identified patent and that said Letters Patent is hereby corrected as shown below:

Specification

In column 14 at line 21, Change "O rings" to --O-rings--.

Signed and Sealed this
Twenty-sixth Day of July, 2016

Michelle K. Lee
*Director of the United States Patent and Trademark Office*